US010342540B2

(12) United States Patent
Smith et al.

(10) Patent No.: US 10,342,540 B2
(45) Date of Patent: Jul. 9, 2019

(54) TISSUE RETRACTION DEVICES AND RELATED METHODS OF USE

(71) Applicant: Boston Scientific Scimed, Inc., Maple Grove, MN (US)

(72) Inventors: Paul Smith, Smithfield, RI (US); Robert Charles, New Boston, NH (US); Jon Taylor, Groton, MA (US); Daniel E. Hamilton, Mont Vernon, NH (US); Samuel Raybin, Marlborough, MA (US); Robert B. Devries, Northborough, MA (US); Niklas Andersson, Wayland, MA (US); Meghan E Soens, Paris (FR); Mary Ann Cornell, Brimfield, MA (US); Ray Tong, Foxborough, MA (US); John Golden, Norton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 218 days.

(21) Appl. No.: 15/284,901

(22) Filed: Oct. 4, 2016

(65) Prior Publication Data
US 2017/0105726 A1 Apr. 20, 2017

Related U.S. Application Data

(60) Provisional application No. 62/241,936, filed on Oct. 15, 2015.

(51) Int. Cl.
*A61B 17/10* (2006.01)
*A61B 17/122* (2006.01)
(Continued)

(52) U.S. Cl.
CPC ............ *A61B 17/10* (2013.01); *A61B 1/0014* (2013.01); *A61B 1/00135* (2013.01);
(Continued)

(58) Field of Classification Search
CPC ... A61B 17/10; A61B 1/00135; A61B 1/0014; A61B 17/00218; A61B 17/04;
(Continued)

(56) References Cited

U.S. PATENT DOCUMENTS 5,423,830 A * 6/1995 Schneebaum .......... A61B 18/10
606/110
5,474,057 A 12/1995 Makower et al.
(Continued)

FOREIGN PATENT DOCUMENTS

KR 2013/0009742 A 1/2013
WO WO 2014/199759 A1 12/2014

OTHER PUBLICATIONS

International Search Report and Written Opinion issued in PCT/US2016/055620, dated Dec. 20, 2016 (11 pages).

*Primary Examiner* — David C Eastwood
(74) *Attorney, Agent, or Firm* — Bookoff McAndrews, PLLC

(57) ABSTRACT

The present disclosure is directed to a medical instrument. The medical instrument may include a delivery device and a retraction mechanism including a target tissue anchor and a first stabilizing anchor, wherein the target tissue anchor attaches to target tissue and connects to the delivery device.

10 Claims, 29 Drawing Sheets

(51) Int. Cl.
*A61B 17/28* (2006.01)
*A61B 17/04* (2006.01)
*A61B 1/00* (2006.01)
*A61B 17/02* (2006.01)
*A61B 17/32* (2006.01)
*A61B 17/00* (2006.01)
*A61B 17/22* (2006.01)

(52) U.S. Cl.
CPC .......... *A61B 17/0218* (2013.01); *A61B 17/04* (2013.01); *A61B 17/122* (2013.01); *A61B 17/28* (2013.01); *A61B 17/320016* (2013.01); *A61B 2017/0034* (2013.01); *A61B 2017/00269* (2013.01); *A61B 2017/00349* (2013.01); *A61B 2017/22069* (2013.01); *A61B 2017/2808* (2013.01)

(58) Field of Classification Search
CPC .................. A61B 17/122; A61B 17/28; A61B 17/320016; A61B 2017/00269; A61B 2017/0034; A61B 2017/00349; A61B 2017/22069; A61B 2017/2808; A61B 17/32056; A61B 17/3207; A61B 2017/320716; A61B 17/320725; A61B 2017/320733; A61B 2017/320741; A61B 17/320783; A61B 17/22; A61B 2017/22001; A61B 2017/22002; A61B 17/22031; A61B 17/22032; A61B 2017/22035; A61B 2017/22051; A61B 2017/22052; A61B 2017/22054; A61B 2017/22055; A61B 2017/22061; A61B 2017/22062; A61B 2017/22064; A61B 2017/22065; A61B 2017/22068; A61B 2017/22081; A61B 2017/22094; A61B 2017/22095; A61B 17/221; A61B 2017/2212; A61B 2017/2217

See application file for complete search history.

(56) References Cited

U.S. PATENT DOCUMENTS

| | | | |
|---|---|---|---|
| 5,683,349 A | 11/1997 | Makower et al. | |
| 5,984,932 A * | 11/1999 | Yoon | A61B 17/0469 606/147 |
| 6,071,233 A * | 6/2000 | Ishikawa | A61B 1/0014 600/104 |
| 6,364,900 B1 * | 4/2002 | Heuser | A61B 17/12109 606/194 |
| 8,454,584 B2 | 6/2013 | Ducharme | |
| 8,945,155 B2 | 2/2015 | Gordin et al. | |
| 9,986,893 B2 * | 6/2018 | Cornhill | A61B 1/00082 |
| 2002/0173819 A1 * | 11/2002 | Leeflang | A61B 17/22 606/200 |
| 2005/0251177 A1 | 11/2005 | Saadat et al. | |
| 2005/0261674 A1 * | 11/2005 | Nobis | A61B 1/00073 606/45 |
| 2006/0009785 A1 * | 1/2006 | Maitland | A61B 17/221 606/113 |
| 2006/0287667 A1 * | 12/2006 | Abela | A61B 17/32075 606/200 |
| 2008/0300594 A1 | 12/2008 | Goto | |
| 2009/0105722 A1 * | 4/2009 | Fulkerson | A61B 17/221 606/127 |
| 2009/0156996 A1 * | 6/2009 | Milsom | A61B 1/00082 604/96.01 |
| 2010/0105983 A1 * | 4/2010 | Oneda | A61B 1/00085 600/115 |
| 2011/0245858 A1 * | 10/2011 | Milsom | A61B 1/00082 606/191 |
| 2012/0059309 A1 * | 3/2012 | di Palma | A61B 17/12186 604/22 |
| 2012/0095291 A1 | 4/2012 | Nakajima | |
| 2013/0184739 A1 * | 7/2013 | Brady | A61B 17/221 606/200 |
| 2013/0184742 A1 * | 7/2013 | Ganesan | A61F 2/01 606/200 |
| 2013/0197515 A1 | 8/2013 | Raybin et al. | |
| 2013/0197567 A1 * | 8/2013 | Brady | A61B 17/221 606/200 |
| 2013/0225934 A1 | 8/2013 | Raybin et al. | |
| 2013/0231677 A1 * | 9/2013 | Carroux | A61B 1/015 606/127 |
| 2013/0274553 A1 * | 10/2013 | Piskun | A61B 1/00154 600/114 |
| 2013/0310803 A1 * | 11/2013 | Morsi | A61B 17/221 604/508 |
| 2015/0250497 A1 * | 9/2015 | Marks | A61B 17/221 606/159 |
| 2015/0265299 A1 * | 9/2015 | Cooper | A61B 17/221 606/200 |
| 2016/0220265 A1 * | 8/2016 | Pokorney | A61B 17/221 |

* cited by examiner

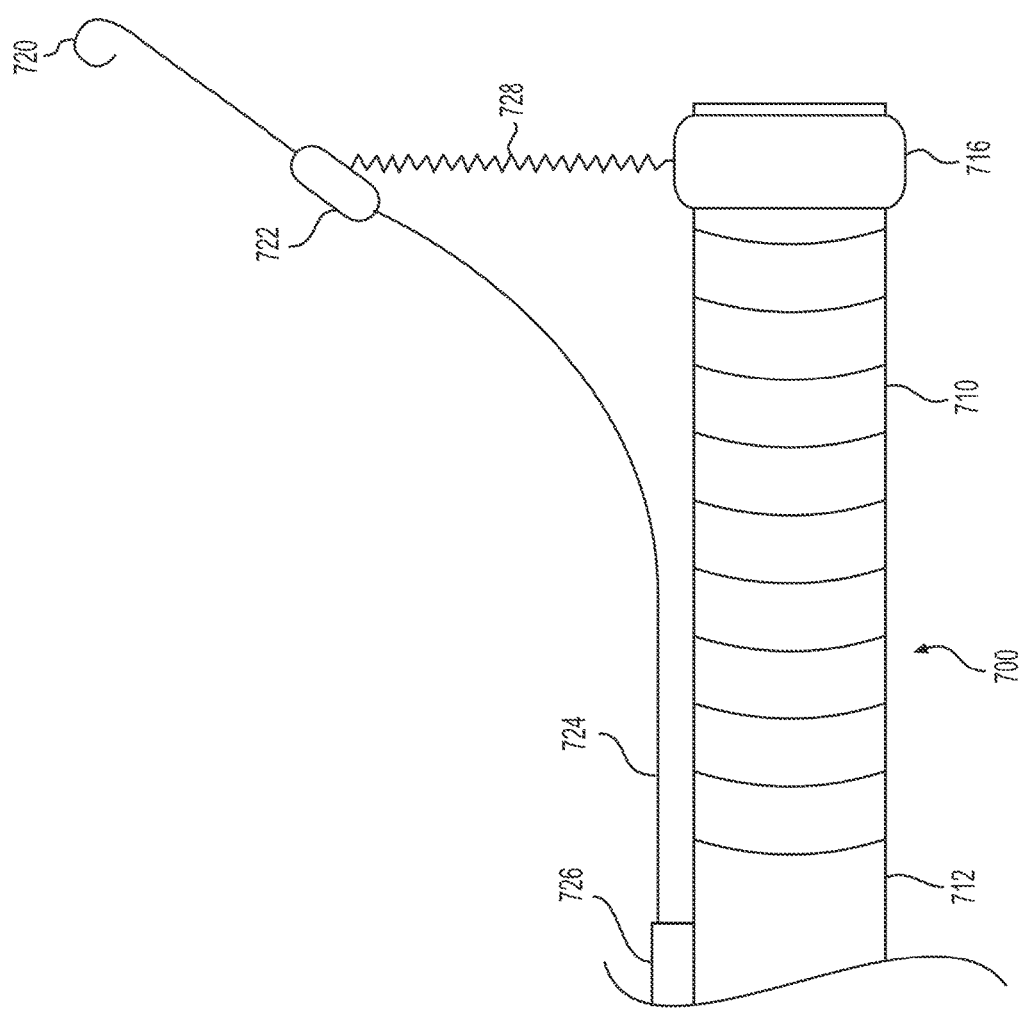

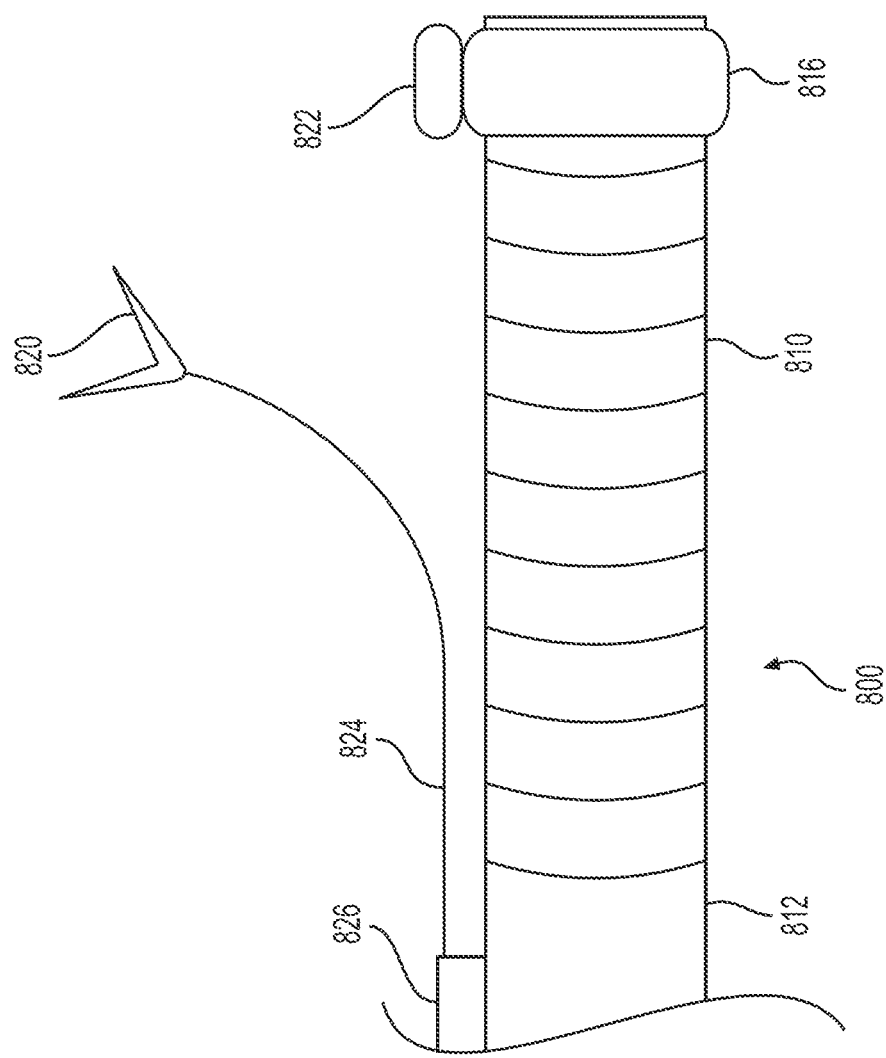

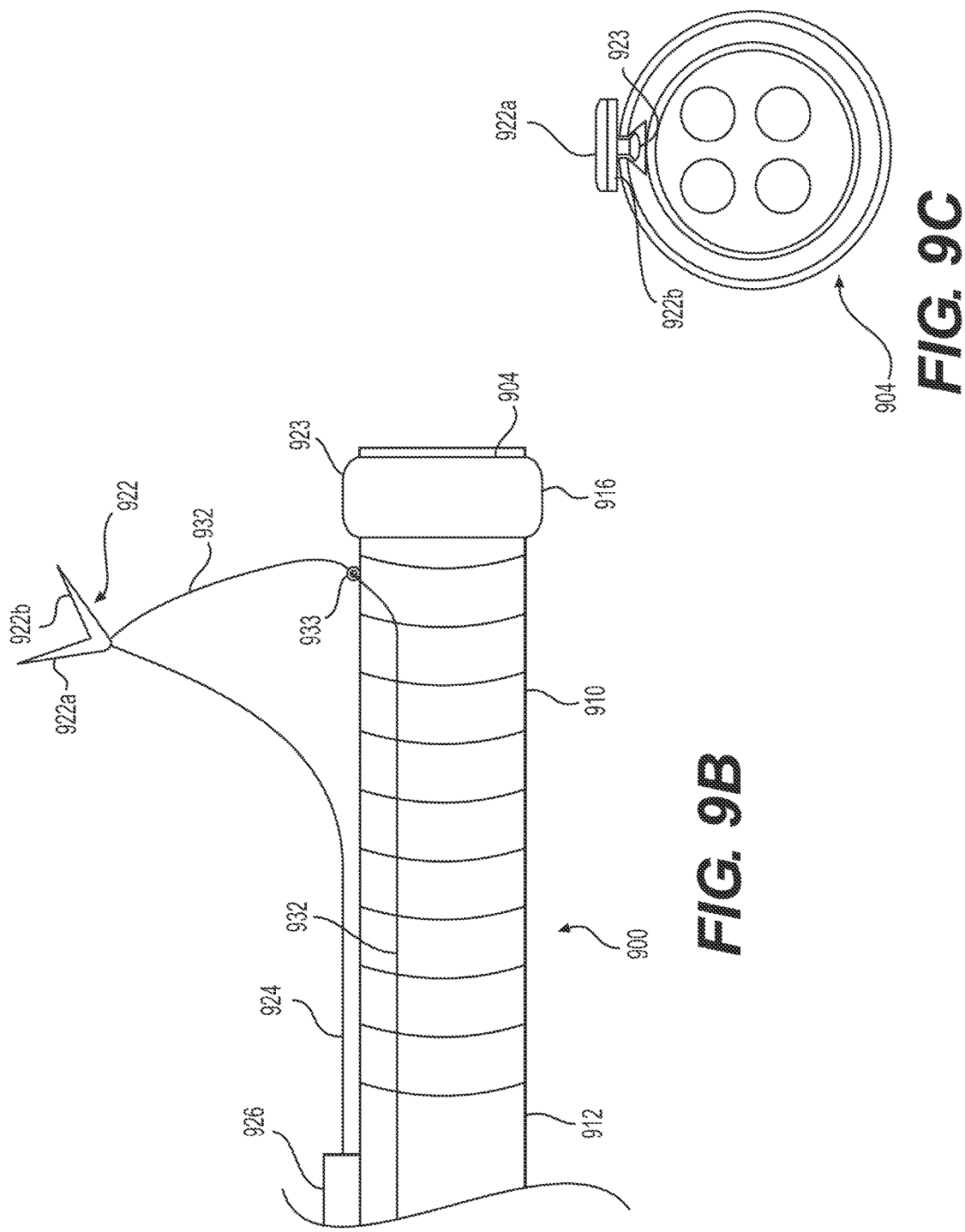

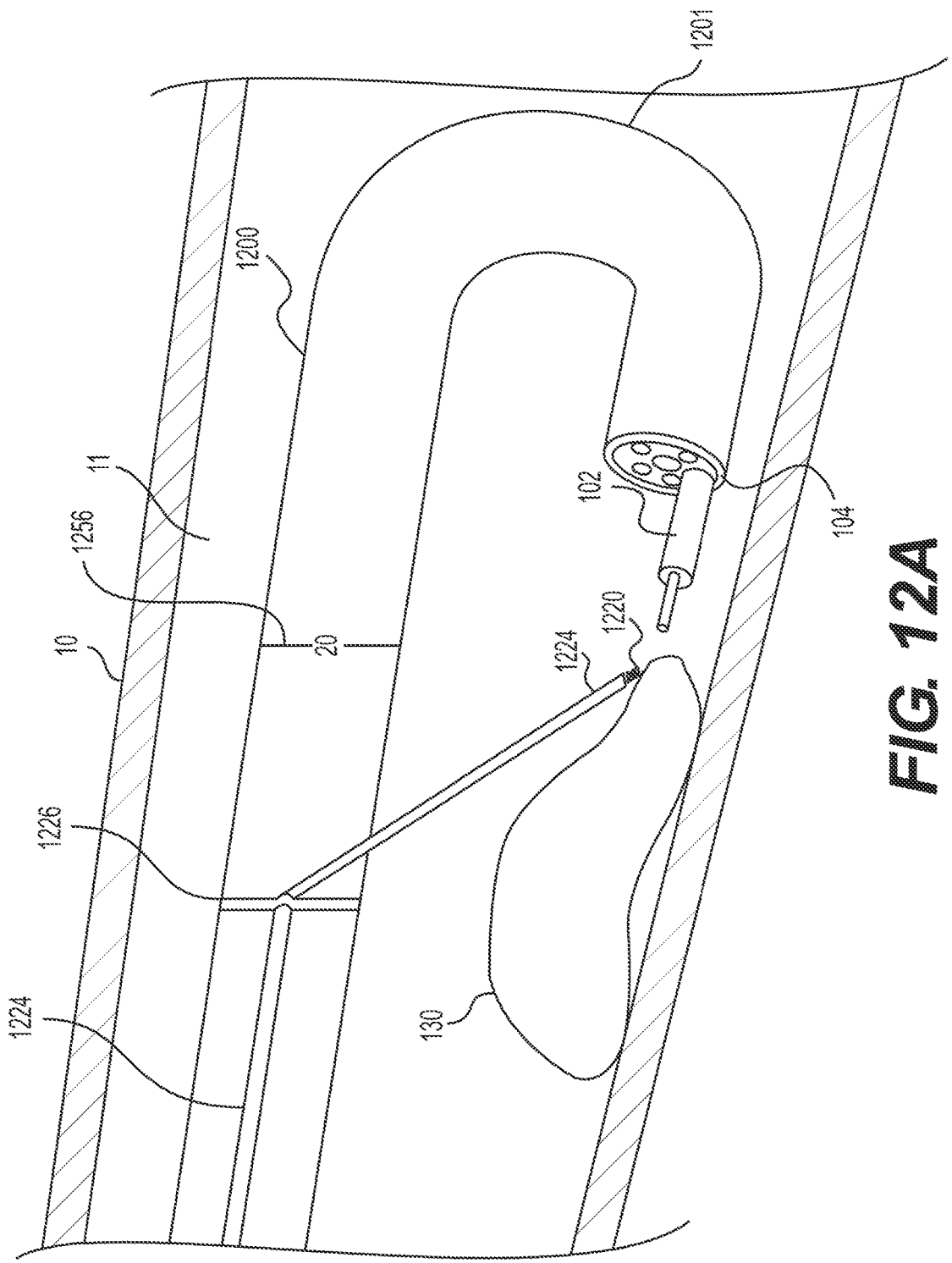

TISSUE RETRACTION DEVICES AND RELATED METHODS OF USE

CROSS-REFERENCE TO RELATED APPLICATIONS

This application claims the benefits of priority from U.S. Provisional Application No. 62/241,936, filed on Oct. 15, 2015, the entirety of which is incorporated herein by reference.

TECHNICAL FIELD

Embodiments of the present disclosure relate generally to medical instruments. More particularly, embodiments of the disclosure relate to medical instruments for use in medical applications, such as, for example, retracting tissue during resection and dissection procedures. Embodiments of the disclosure also cover methods of using such instruments.

BACKGROUND OF THE DISCLOSURE

Physicians have become increasingly willing to perform more aggressive interventional and therapeutic endoscopic procedures, including the removal of larger lesions (both noncancerous and cancerous). In gastrointestinal, colonic, and esophageal cancer, for example, lesions or cancerous masses may form along the mucosa and often extend into the lumens of the organs. Conventionally, the condition is treated by cutting out a portion of the affected organ wall. Physicians have adopted minimally invasive techniques called endoscopic mucosal resection (EMR) and endoscopic submucosal dissection (ESD). EMR methods are typically used for removal of small cancerous or abnormal tissues (e.g., polyps), and ESD methods are typically used for en bloc removal of large cancerous or abnormal tissues (e.g., lesions). These procedures are generally performed with a delivery device (e.g. an endoscope). During these procedures, the mucosal layer containing the lesion is generally separated from the underlying tissue layers using a medical instrument extending through a working channel of the delivery device. As the medical instrument dissects or resects the tissue, however, the resulting tissue "flap" (e.g., already-resected portion of the mucosal layer) often obstructs the medical instrument from accessing and removing the remainder of the lesion.

As such, there exists a need for a device that provides both tissue retraction and precise cutting. In particular, there is a need for devices that can retract tissue independently of the movement of the delivery device. Such a device would allow operators to use the delivery device tip deflection to direct the cutting instruments without simultaneous moving the tissue.

SUMMARY OF THE DISCLOSURE

Aspects of the present disclosure relate to, among other things, retractors. Each of the aspects disclosed herein may include one or more of the features described in connection with any of the other disclosed aspects.

According to one aspect of the present disclosure, a medical instrument may include a delivery device, and a retractor including a target tissue anchor and a first stabilizing anchor, wherein the target tissue anchor attaches to target tissue and connects to the delivery device.

Additionally or alternatively, the medical instrument may include one or more other features describe here. For example, the first stabilizing anchor may attach to a portion of a body wall of a patient distal to the delivery device. In another example, a tension mechanism may connect the target tissue anchor and the first stabilizing anchor, and the tension mechanism may include at least one of a spring, a string, a wire, a rod, a pulley, and an elastic band. The delivery device may include an overtube and the retractor may be at least partially disposed in the overtube. The first stabilizing anchor may have an expanded configuration and a contracted configuration. The first stabilizing anchor may be one of an inflatable balloon or an expandable structure comprised of a plurality of wires. The delivery device may include an articulation section, and the first stabilizing anchor attaches to the delivery device proximal of the articulation section. The target tissue anchor may be one of a clip, a suture, a corkscrew, a spike, a hook, a grasper, a staple, an adhesive, a loop, a spiral loop, or a helical loop. The target tissue anchor may connect to a proximal end of the delivery device. The medical instrument may further include a second stabilizing anchor, and the first stabilizing anchor may attach to a body wall of a patient, and the second stabilizing anchor may attach to the delivery device. A distal end of the delivery device may move independently of the retractor when the retractor is connected to the delivery device. The retractor may have an insertion configuration and a retracting configuration, and releasing the target tissue anchor from a position proximate the delivery device to a position farther away from the delivery device may transition the retractor from the insertion configuration to the retracting configuration. The target tissue anchor may transition between the insertion configuration and the retracting configuration via an actuator at a proximal end of the delivery device. The delivery device may be adapted to deliver a cutting instrument configured to cut the target tissue and the retractor may be adapted to pull a portion of the target tissue away from a body wall of a patient. When in an expanded configuration, the stabilizing anchor may be adapted to remain in one location relative to a body wall of a patient, and the tension mechanism may be adapted to pull the target tissue toward the stabilizing anchor and away from the body wall.

According to another aspect of the present disclosure, a retractor may include a target tissue anchor, wherein the target tissue anchor may be adapted to attach to target tissue, a stabilizing anchor, wherein the stabilizing device has an expanded configuration and a contracted configuration and is adapted to contact tissue distal the target tissue at a plurality of points, and a tension mechanism connecting the target tissue anchor and the stabilizing anchor.

Additionally or alternatively, the retractor may include one or more other features described here. For example, when in the expanded configuration, the stabilizing anchor may be adapted to remain in one location relative to a body wall of a patient, and the tension mechanism may be adapted to pull the target tissue toward the stabilizing anchor and away from the body wall. The first stabilizing anchor may be one of an inflatable balloon or an expandable structure comprised of a plurality of wires.

According to another aspect of the present disclosure, a medical instrument may include a delivery device and a retractor including a target tissue anchor and a first stabilizing anchor, wherein the target tissue anchor may be adapted to attach to target tissue and connect to the delivery device, and the stabilizing device may be adapted to attach to the delivery device.

Additionally or alternatively, the medical instrument may include one or more other features described here. For example, the delivery device may be adapted to deliver a cutting instrument configured to cut the target tissue, and the retractor may be adapted to pull a portion of the target tissue away from a body wall of a patient.

Additional objects and advantages of the disclosed aspects will be set forth in part in the description that follows, and in part will be apparent from the description, or may be learned by practice of the disclosed aspects. The objects and advantages of the disclosed aspects will be realized and attained by means of the elements and combinations particularly pointed out in the appended claims.

It is to be understood that both the foregoing general description and the following detailed description are exemplary and explanatory only and are not restrictive of the scope of disclosed aspects, as set forth by the claims.

BRIEF DESCRIPTION OF THE DRAWINGS

The accompanying drawings, which are incorporated in and constitute a part of this specification, illustrate embodiments of the disclosure and together with the description, serve to explain the principles of the disclosure.

FIGS. 9A-C illustrate an alternative exemplary delivery device having a retraction mechanism anchored to the delivery device proximal to an articulation section.

FIGS. 12A-C illustrate an exemplary retroflexed delivery device having a retraction mechanism anchored to the delivery device proximal to an articulation section.

DETAILED DESCRIPTION

Reference will now be made in detail to embodiments of the present disclosure, examples of which are illustrated in the accompanying drawings. Wherever possible, the same reference numbers will be used throughout the drawings to refer to the same or like parts. The term "distal" refers to the end farthest away from a user when introducing a device into a patient. The term "proximal" refers to the end closest to the user when placing the device into the patient. When used herein, the terms "approximately" and "substantially" may indicate a range of values within +/−5% of a stated value.

Embodiments of the present disclosure relate to systems and methods for retracting portions of target tissue that have been separated from any underlying tissue layers. For example, the device may retract tissue layers that have been separated from the mucosal walls of the colon, esophagus, stomach, or duodenum, facilitating the continued resection of undesired tissue.

Figure 1:
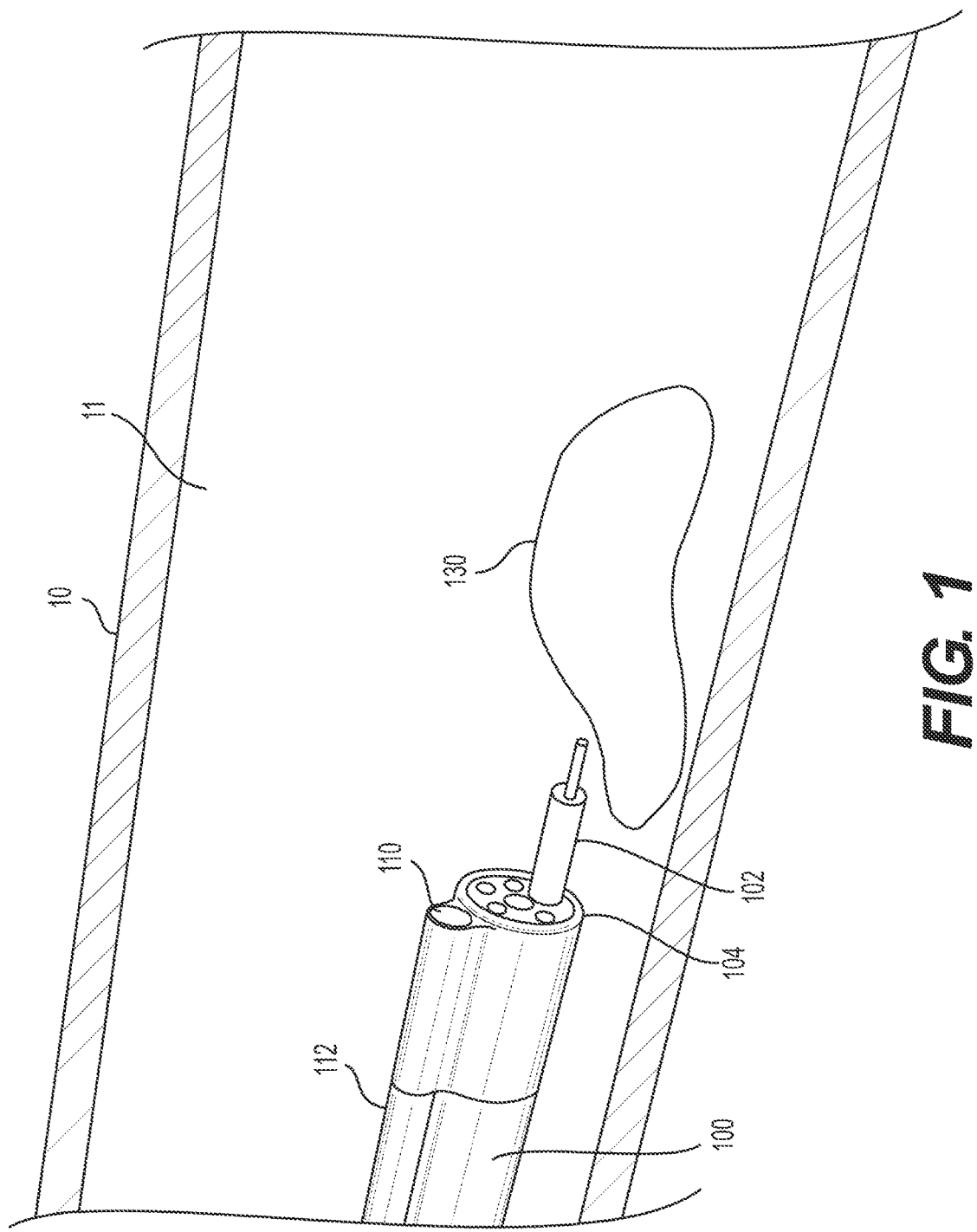
FIG. 1 illustrates a distal portion of an exemplary delivery device including a cutting instrument and an overtube.

An exemplary body wall 10 of an anatomical lumen 11, and undesired/target tissue 130, are illustrated in FIG. 1. FIG. 1 further depicts a delivery device 100 (e.g., an endoscope, sheath, catheter, etc.) positioning within a patient body medical instruments for grasping, resecting, retracting, and/or otherwise manipulating tissue. Delivery device 100 may be used for procedures within or adjacent to various body organs (e.g., including body wall 10), such as, an esophagus, a heart, a stomach, a pelvic area, a bladder, an intestine, or any other portion of a gastrointestinal, urinary, or pulmonary tract. Delivery device 100 may be configured for insertion into a patient's body through an anatomical opening. In some embodiments, delivery device 100 may be used in natural orifice transluminal endoscopic surgery (NOTES) procedures or single incision laparoscopic surgical (SILS) procedures. Accordingly, delivery device 100 may be shaped and sized for placement into a patient via a body cavity or an incision.

Delivery device 100 includes a proximal end (not shown) and a distal end 104. Delivery device 100 may include one or more working channel(s) (e.g., a single working channel or multiple channels as shown in FIG. 1) extending substantially longitudinally (axially) between the proximal end and the distal end 104 of delivery device 100. The one or more working channels may have any suitable size, cross-sectional area, shape, and/or configuration to, for example, introduce medical instruments (e.g., resection tools) to distal end 104 of delivery device 100. In some embodiments, the working channel(s) may be made of, or coated with, a polymeric or lubricious material to enable the introduced medical instruments to pass through the working channel(s) with ease.

Delivery device 100 may be a flexible tube, made from any suitable biocompatible material known to one of ordinary skill in the art and having sufficient flexibility to traverse tortuous anatomy. Such materials may include, but are not limited to, rubber, silicon, synthetic plastic, stainless steel, metal-polymer composites, and metal alloys of nickel, titanium, copper cobalt, vanadium, chromium, and iron. In some examples, the material forming delivery device 100 may be a superelastic material such as nitinol, which is a nickel-titanium alloy. In some embodiments, delivery device 100 may include layers of different materials and reinforcements. Delivery device 100 may have any cross-sectional shape and/or configuration and may be any desired dimension that can be received in a body cavity. In some embodiments, delivery device 100 may be made of, or coated with, a polymeric or lubricious material to enable delivery device 100 to pass through a body cavity with ease. Additionally, delivery device 100 may be steerable and may have areas of different flexibility or stiffness to promote steerability within the body cavity. Delivery devices 700, 800, 900, 1000, 1100, 1200, 1600, and/or 1700 may include any of the features and/or components of delivery device 100.

Medical instrument 102 may be slidably inserted and advanced through one of the working channel(s) of delivery device 100. Medical instrument 102 may be configured for use during a surgical method. Medical instrument 102 may be configured for use during diagnostic and/or therapeutic procedures, including dissection procedures such as, for example, endoscopic mucosal resection (EMR) and endoscopic submucosal dissection (ESD) procedures. As tissue is resected from the body by the chosen procedure and/or by medical instrument 102, the already-resected tissue may obstruct medical instrument 102's ability to reach and/or remove the remaining target tissue. As such, a tissue retraction mechanism may be used to lift/pull the already-resected tissue out of the way (e.g. radially inward from body wall 10 and/or distally of medical instrument 102). Conventional target tissue anchors, however, are affected by the movement of the delivery device. Thus, as the operator moves the delivery device, the already-resected tissue also moves. The present disclosure includes various tissue retraction mechanisms with tissue retraction capabilities that are not affected by delivery device tip movement. Such tissue retraction capabilities may be achieved in a variety of ways, including, but not limited to, anchoring the tissue retraction mechanism. The tissue retraction mechanism may be anchored, for example, to (1) the patient's body (e.g., body wall 10) distal the target tissue and/or (2) the delivery device, proximal of the delivery device's articulation section.

1. Anchoring a Retraction Mechanism to a Body, Distal the Target Tissue

Figure 2:
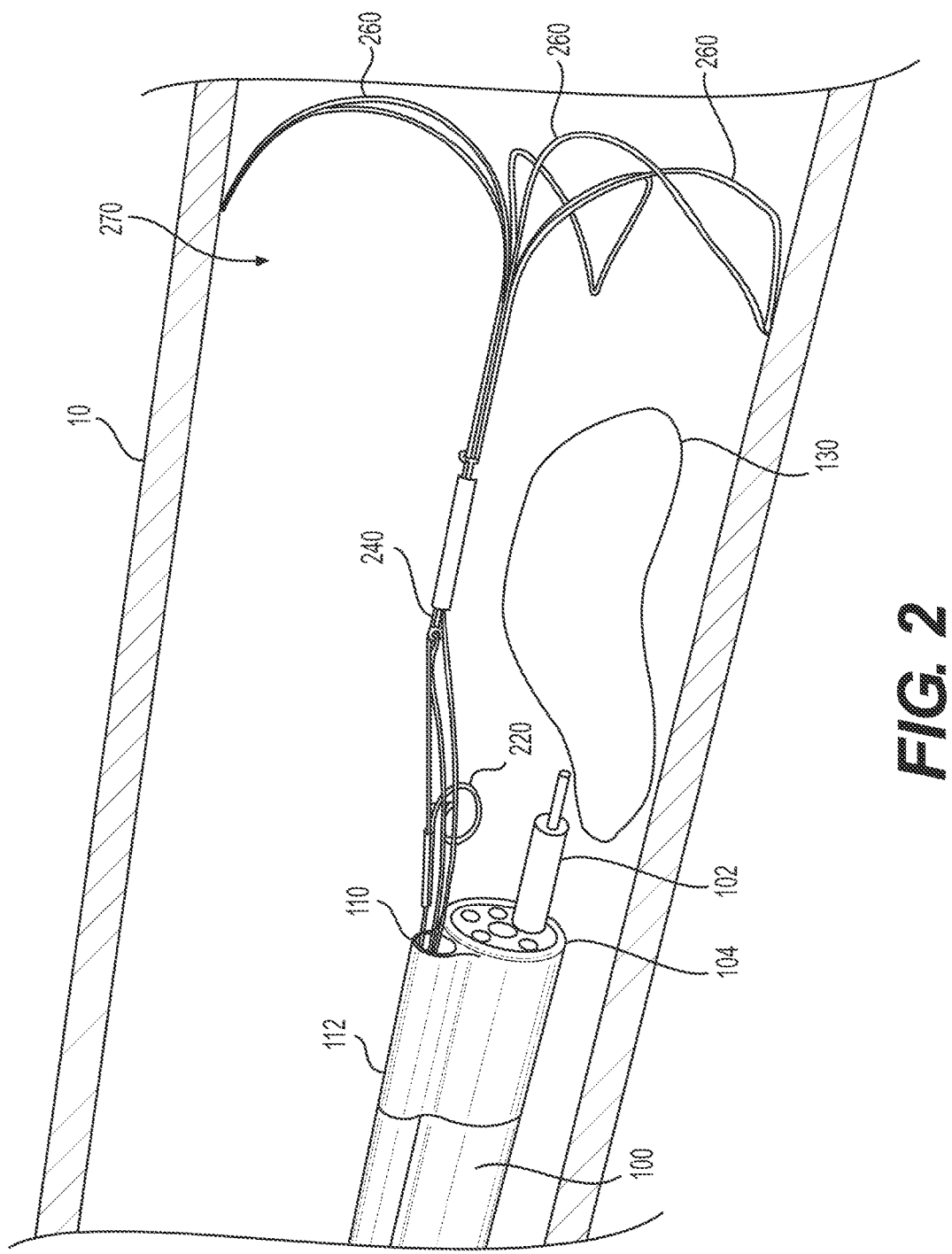
FIG. 2 illustrates a distal portion of an exemplary delivery device including a cutting instrument, an overtube, and an exemplary stabilizing anchor in an expanded configuration.

In some examples, a retractor/tissue retraction mechanism may be anchored to body wall 10, distal the target tissue 130. FIG. 2 illustrates one such example. In FIG. 2, delivery device 100 includes overtube 112. Overtube 112 may be connected to delivery device 100 in any way, including, but not limited to, being integral with delivery device 100, attached at discrete locations along delivery device 100, or connected to delivery device 100 via a sleeve. Overtube 112 may extend between the proximal end of delivery device 100 and the distal end 104. Overtube 112 may be a flexible tube, made from any suitable biocompatible material known to one of ordinary skill in the art and having sufficient flexibility to traverse tortuous anatomy in unison with delivery device 100 and/or move in the same direction that delivery device 100 is steered. Such materials may include, but are not limited to, rubber, silicon, synthetic plastic, stainless steel, metal-polymer composites, and metal alloys of nickel, titanium, copper cobalt, vanadium, chromium, and iron. In some examples, the material forming overtube 112 may be a superelastic material such as nitinol, which is a nickel-titanium alloy. In some embodiments, overtube 112 may include layers of different materials and reinforcements. In some examples, delivery device 100 and overtube 112 may be formed of the same material. In other examples, delivery device 100 and overtube 112 may be formed of different materials. Overtube 112 may have any cross-sectional shape and/or configuration and may be any desired dimension that can be received in a body cavity and/or connected to delivery device 100. In some embodiments, overtube 112 may be made of, or coated with, a polymeric or lubricious material to enable overtube 112 to pass through a body cavity with ease. Additionally, delivery device 100 may be steerable and may have areas of different flexibility or stiffness to promote steerability within the body cavity. In examples in which overtube 112 is attached to delivery device 100, overtube 112 may move with delivery device 100 as it is steered.

Overtube 112 may include one or more channels 110. The one or more channels 110 may extend substantially longitudinally (axially) within overtube 112, and generally between the proximal end and distal end 104 of delivery device 100. The one or more channels 110 may have any suitable size, cross-sectional area, shape, and/or configuration to, for example, introduce medical instruments (e.g., target tissue anchor(s) and/or stabilizing anchor(s) as described below) to distal end 104 of delivery device 100. In some embodiments, channels 110 may be made of, or coated with, a polymeric or lubricious material to enable the introduced medical instruments to pass through channel(s) 110 with ease. In some examples, delivery device 100 may not include an overtube. In such examples, medical instruments, such as target tissue anchor(s) and/or stabilizing anchor(s), may be introduced through one of the working channels of delivery device 100.

A retractor, also called a tissue retraction mechanism, may be introduced into a human body via a delivery device. The tissue retraction mechanism may include target tissue anchor(s), stabilizing anchor(s), and/or tension mechanism(s). A target tissue anchor may be any mechanism capable of grasping, securing, and/or manipulating tissue. For example, the target tissue anchor may be a clip, suture, corkscrew, spike, hook, grasper, staple, adhesive, simple loop (e.g., loop 620 of FIG. 6), spiral loop, helical loop, etc. The attachment of the target tissue anchor to the target tissue may need to be proximal of the proximalmost portion of a stabilizing anchor, so that the entire target tissue may be retracted distally from the cutting zone until the entire target tissue has been excised.

A stabilizing anchor may be any mechanism capable of anchoring a target tissue anchor to a body wall, including, for example, a wire petal (e.g., wire petal 260 of FIGS. 2 and 3), a wire bulb (e.g., wire bulb 460 of FIG. 4), a stent (e.g. stent 560 of FIG. 5), an expandable member (e.g., expandable member 670 of FIG. 6), a loop, a clip, suture, corkscrew, spikes, hooks, grasper, staple, adhesive, etc. The target tissue anchor may be connected to the stabilizing anchor via, for example, an elongate connector, including wire(s) and/or a tension mechanism. The tension mechanism may be any mechanism capable of providing tension on the retracted tissue, including, but not limited to, springs (e.g., spring 540 of FIG. 5), elastic bands, and/or a string/wire/rod/pulley system controlled by an operator (e.g., a pulley system or loop 240 of FIG. 2). The target tissue anchor and the stabilizing anchor may be deployed from distal end 104 of delivery device 100 through a working channel or channel 110 of overtube 112. Once deployed, a stabilizing anchor may contact and secure to a body wall, e.g., body wall 10. Specific examples of target tissue anchors, stabilizing anchors, and tension mechanisms for anchoring a retraction mechanism to a body wall will be described in more detail below with respect to FIGS. 2-6. The retraction mechanisms of the present disclosure are not limited to specific combinations disclosed herein. Each of the below-described (1) target tissue anchors, (2) stabilizing anchors, and (3) tensions mechanisms may be used in any combination.

Figure 3:
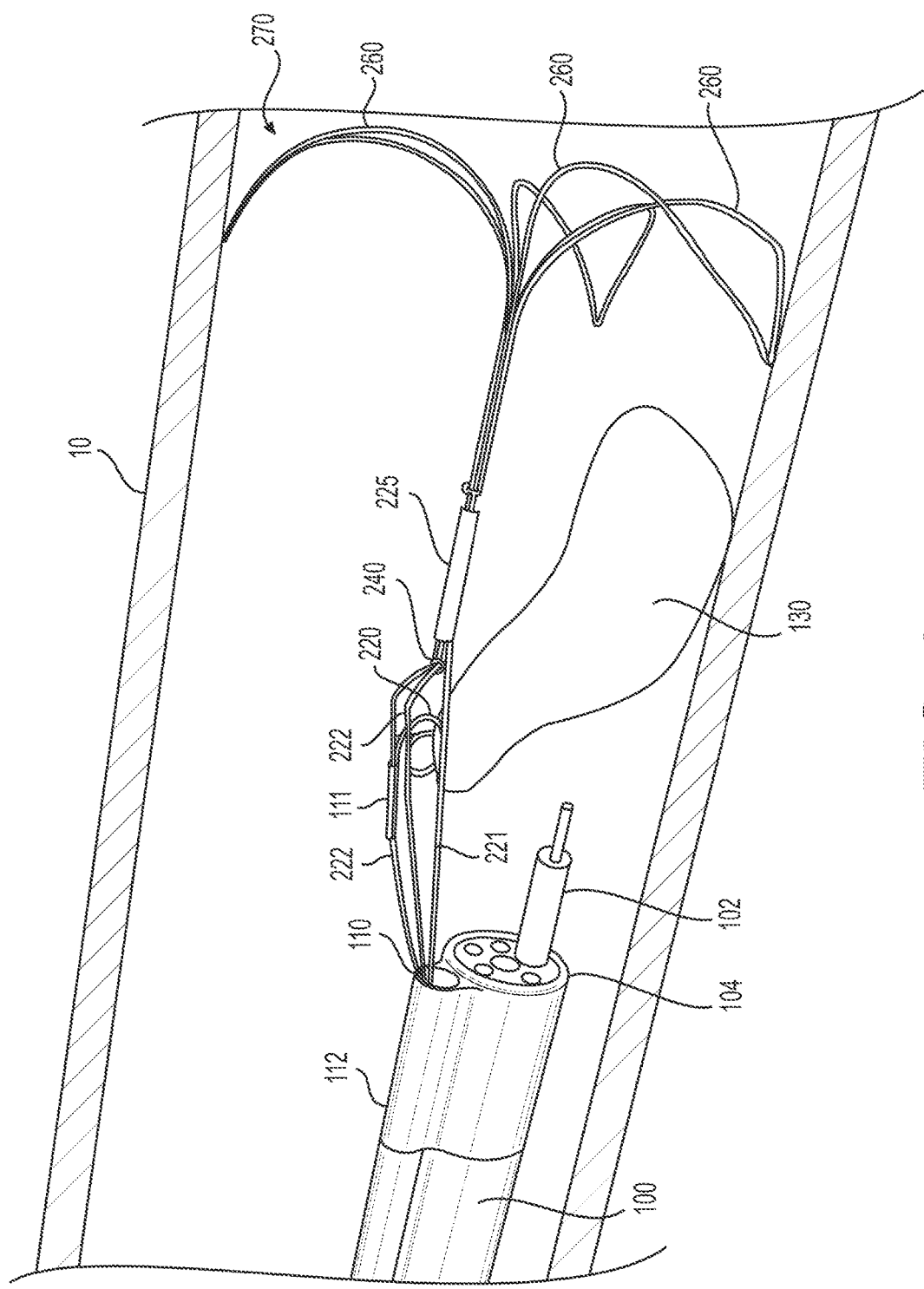
FIG. 3 illustrates an exemplary retraction mechanism retracting a portion of the target tissue.

In the example illustrated in FIG. 2, target tissue anchor 220 and stabilizing anchor 260 have been extended distally through channel 110. Target tissue anchor 220 is spiral loop-shaped (an exemplary spiral loop-shaped target tissue anchor is described in greater detail below with respect to FIGS. 11A-C), tension mechanism 240 is a pulley system, and stabilizing anchor 270 is in a petal configuration. Stabilizing anchor 270 may include any number, configuration, size, and/or shape of petals 260. For example, though FIGS. 2-3 illustrate three petals, any suitable number of petals may be used. Petals 260 may be connected at their proximal ends and/or each petal may have a concave shape relative to the proximal direction. Stabilizing anchor 270 may be configured to transition between a first contracted configuration (e.g., for insertion) and a second expanded configuration (e.g., once in a desired position relative to target tissue 130). Stabilizing anchor 270 may be in the contracted configuration during delivery to and/or positioning at the target tissue 130. In the contracted configuration, stabilizing anchor 270 has a cross-sectional area capable of being slidably disposed within channel 110. In the expanded configuration, petals 260 may project radially outward to contact body wall 10. Petals 260 of stabilizing anchor 270 may contact body wall 10 with sufficient pressure to secure stabilizing anchor 270 in place and/or counteract any proximal pulling by tension mechanism 240. Petals 260 may have rounded ends and/or pointed ends (as shown in FIG. 2). Pointed ends may aid in anchoring petals 260 and holding the stabilizing anchor 270 and/or target tissue anchor 220 in a desired location. In some examples, the ends of petal 260 may be sufficiently sharp to penetrate body wall 10.

Expansion of petals 260 from a contracted configuration to an expanded configuration may be due to, for example, inherent outward biasing, deformation due to body heat (e.g., stabilizing anchor 270 may be formed of shape memory material, such as, a superelastic material), or the like. In some examples, expansion of petals 260 may be due to a deployment mechanism, such as a pull-wire or pulley mechanism whereupon the operator pulls an attached wire that can expand or contract petals 260. In other examples, the interior walls of channel 110 may hold petals 260 in the contracted configuration until stabilizing anchor 270 is pushed distally or delivery device 100 is pulled proximally, thus allowing petals 260 to transition to their natural, expanded configuration upon removal from channel 110.

Figure 11A:
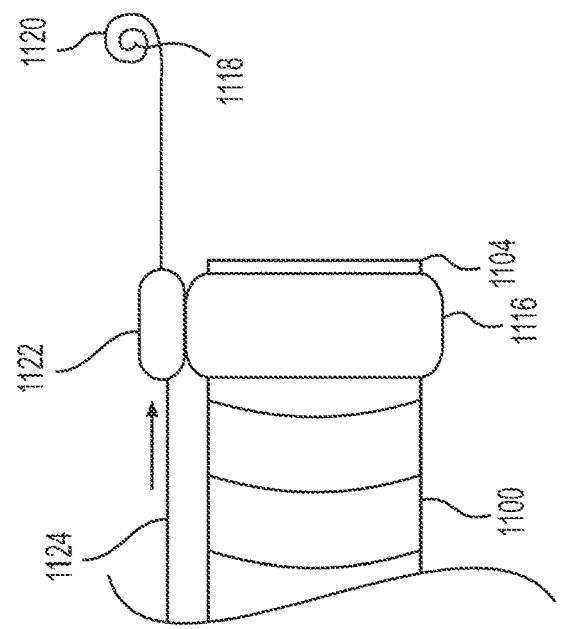
FIGS. 11A-C illustrate an exemplary target tissue anchor transitioning from an insertion configuration to an engaged configuration.
Figure 11B:
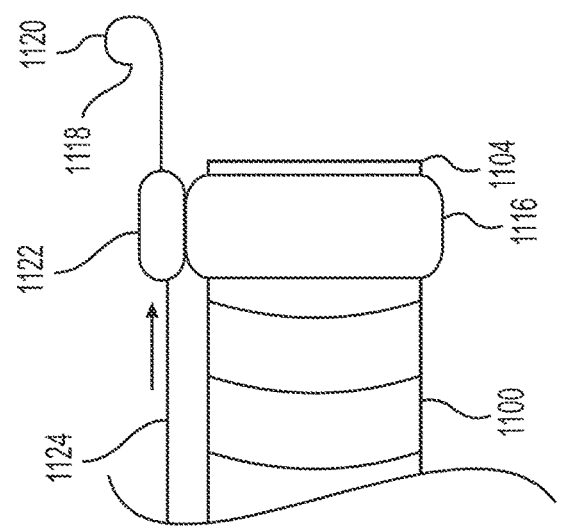
Figure 11C:
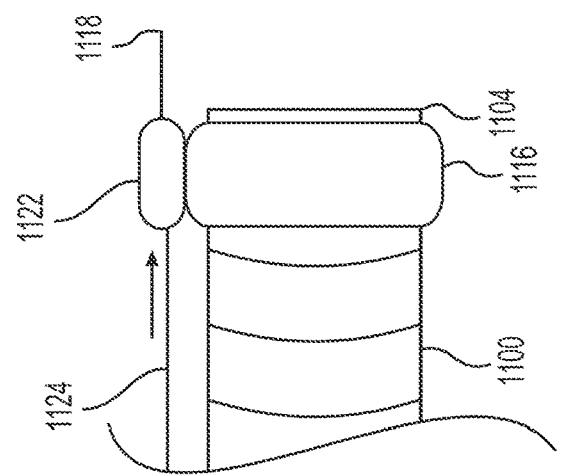

FIG. 3 illustrates target tissue anchor 220 secured to and retracting a previously resected portion of target tissue 130 (e.g., a flap). FIGS. 11A-C illustrate one example of how such a target tissue anchor may transition from a straight configuration (e.g., an insertion configuration for travelling through channel 110) to the spiral loop-shape shown in FIG. 3. For example, in order to secure target tissue 130 with target tissue anchor 220, channel 110 may be positioned proximate to target tissue 130. Target tissue anchor 220 extends distally of the distal end of channel 110 in a straight configuration (see FIG. 11A). The distal end of the target tissue anchor 220 may be configured to pierce the target tissue. As the target tissue anchor 220 is extending further distally of the distal end of channel 110, target tissue anchor 220 may extend distally of the target tissue 130 and may begin to curve in the proximal direction back toward and/or through target tissue 130 (see FIG. 11B). For example, the operator may have positioned target tissue anchor 220 so that when it transitions to the engaged position (e.g., transitioning from FIG. 11A to FIG. 11C), the sharp distal end of target tissue anchor 220 pierces and secures target tissue 130.

In the example illustrated in FIG. 3, cutting instrument 102 may have already cut through a proximal portion of the target tissue 130, leaving a flap. A tissue retraction mechanism is used to pull this flap radially inward of the attached body wall and provide a clear working area for cutting instrument 102 to cut the remainder of target tissue 130 from body wall 10.

In the example shown in FIG. 3, wire 222 may be connected with, and extend through, tension mechanism 240 (e.g., a pulley system or turning loop). A first portion of wire 222 may extend through channel 110 to tension mechanism 240 and a second portion of wire 222 may extend proximally from tension mechanism 240 and into channel 110 to the proximal end of overtube 112. In some examples, tube 111 may fixedly attach to a section of wire 222 and to target tissue anchor 220. Using a portion of wire 222 that is positioned at the proximal end of overtube 112 and manipulable by an operator, the operator may position tube 111 exterior to overtube 112 near target tissue 130 and/or within the field of view of delivery device 100 (as described in further detail below with respect to FIGS. 11A-C). Upon exiting overtube 112 (as described above) target tissue anchor 220 may transition from a straight configuration (see FIG. 11A) to an engaged configuration (see FIG. 11C) and/or the distal end of the target tissue anchor 220 may pierce the target tissue. Once target tissue anchor 220 secures to target tissue 130, an operator may use an end of wire 222 that is at the operator end of the overtube 112 to control the amount of tension and/or the distance the previously-resected portion of target tissue 130 is pulled up (inward) and/or distally. For example, the more an operator proximally pulls an end of wire 222, the further the already-resected portion of target tissue 130 will be pulled distally.

In some examples, the device may include wire 221. Wire 221 may be used as an additional tether for the stabilizing anchor, as additional support, to transition the stabilizing anchor to a contracted configuration, and/or to pull the stabilizing anchor into channel 110. In some examples, the device may include sleeve 225. Wire 221 may extend from channel 110 into sleeve 225. Sleeve 225 may aid in stabilizing the device and holding connecting wires in a single bundle.

Figure 4:
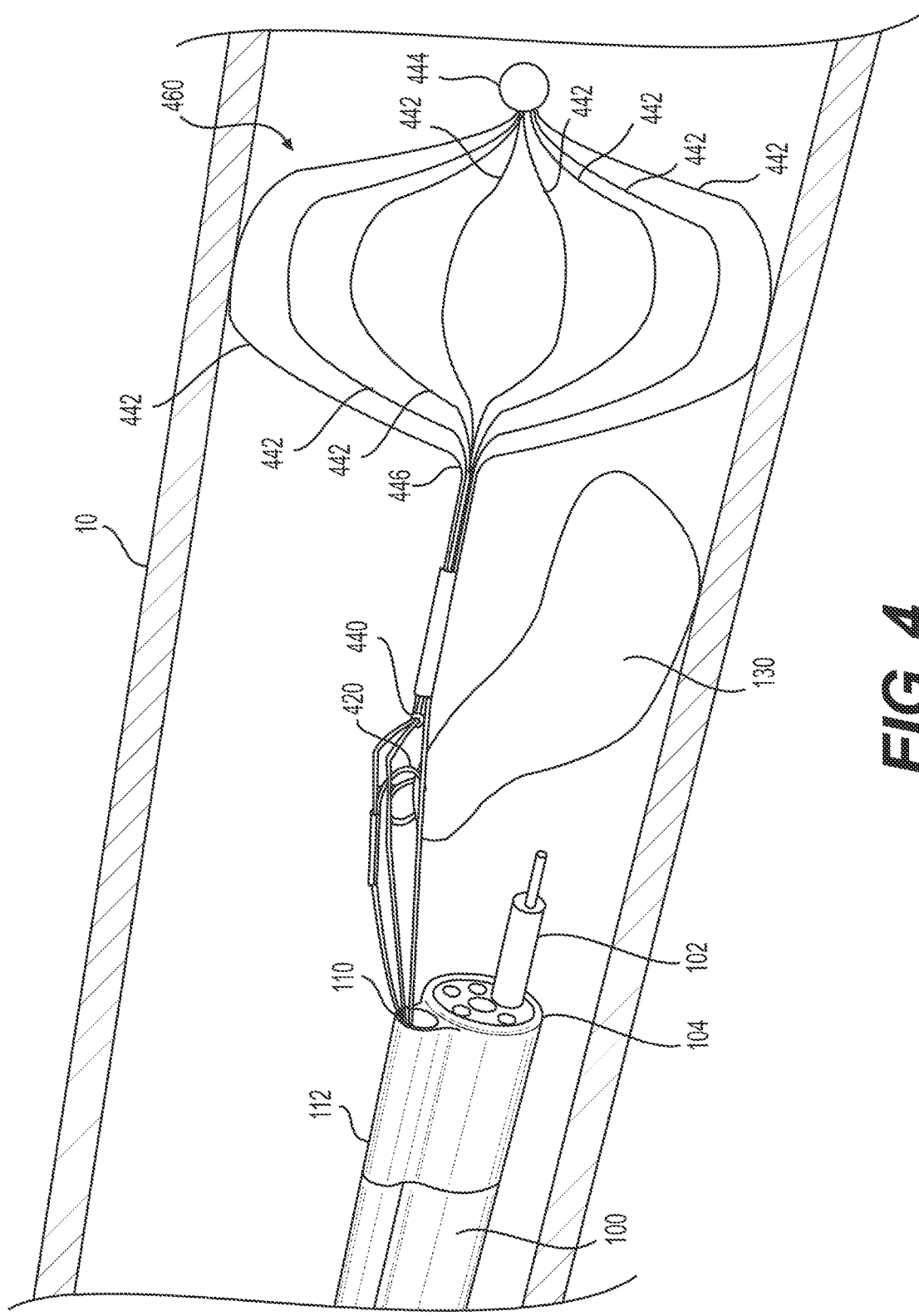
FIG. 4 illustrates an exemplary alternative retraction mechanism retracting a portion of the target tissue.

FIG. 4 illustrates an alternative example of anchoring a retraction mechanism to a body wall. In the example illustrated in FIG. 4, target tissue anchor 420 is a spiral loop similar to target tissue anchor 220 of FIGS. 2 and 3 and/or target tissue anchor 1120 of FIG. 11. Tension mechanism 440 is a pulley system similar to the tension mechanism 240 of FIGS. 2 and 3. Stabilizing anchor 460 is a wire bulb having a basket-like configuration. Each of legs 442 of wire bulb 460 may be connected at a proximal end 446 and a distal end 444. In some examples, legs 442 may be connected at only one end of bulb 460, e.g., only proximal end 446 or distal end 444. As shown in FIG. 4, distal end 444 may be a round, blunt end—an atraumatic tip. Legs 442 may be radially spaced about the longitudinal axis of bulb 460. FIG. 4 shows eight legs, but bulb 460 may have any suitable number of legs. Legs 442 may include barbs, spikes, and/or other features to further anchor bulb 460 into body wall 10. Stabilizing anchor 460 may be configured to transition between a first contracted configuration (e.g., for insertion) and a second expanded configuration (e.g., once in a desired position relative to target tissue 130). Stabilizing anchor 460 may be in the contracted configuration during delivery to and/or positioning at the target tissue 130. In the contracted configuration, stabilizing anchor 460 has a cross-sectional area capable of sliding within channel 110. In the expanded configuration, legs 442 of wire bulb 460 may project radially outward to contact and secure to body wall 10. Expansion of legs 442 from a contracted configuration to an expanded configuration may be due to, for example, inherent outward biasing, deformation due to body heat (e.g., stabilizing anchor 460 may be formed of shape memory material, such as, a superelastic material), or the like. In some examples, expansion of bulb 460 may be due to a deployment mechanism, such as a pull-wire or pulley mechanism whereupon the operator pulls an attached wire that can expand or contract bulb 460. For example, the additional pull-wire or pulley mechanism may be attached to distal end 444, pushing distal end 444 distally may transition wire bulb 460 into the contracted configuration and pulling distal end 444 proximally may expand wire bulb 460 into the expanded configuration.

Figure 5:
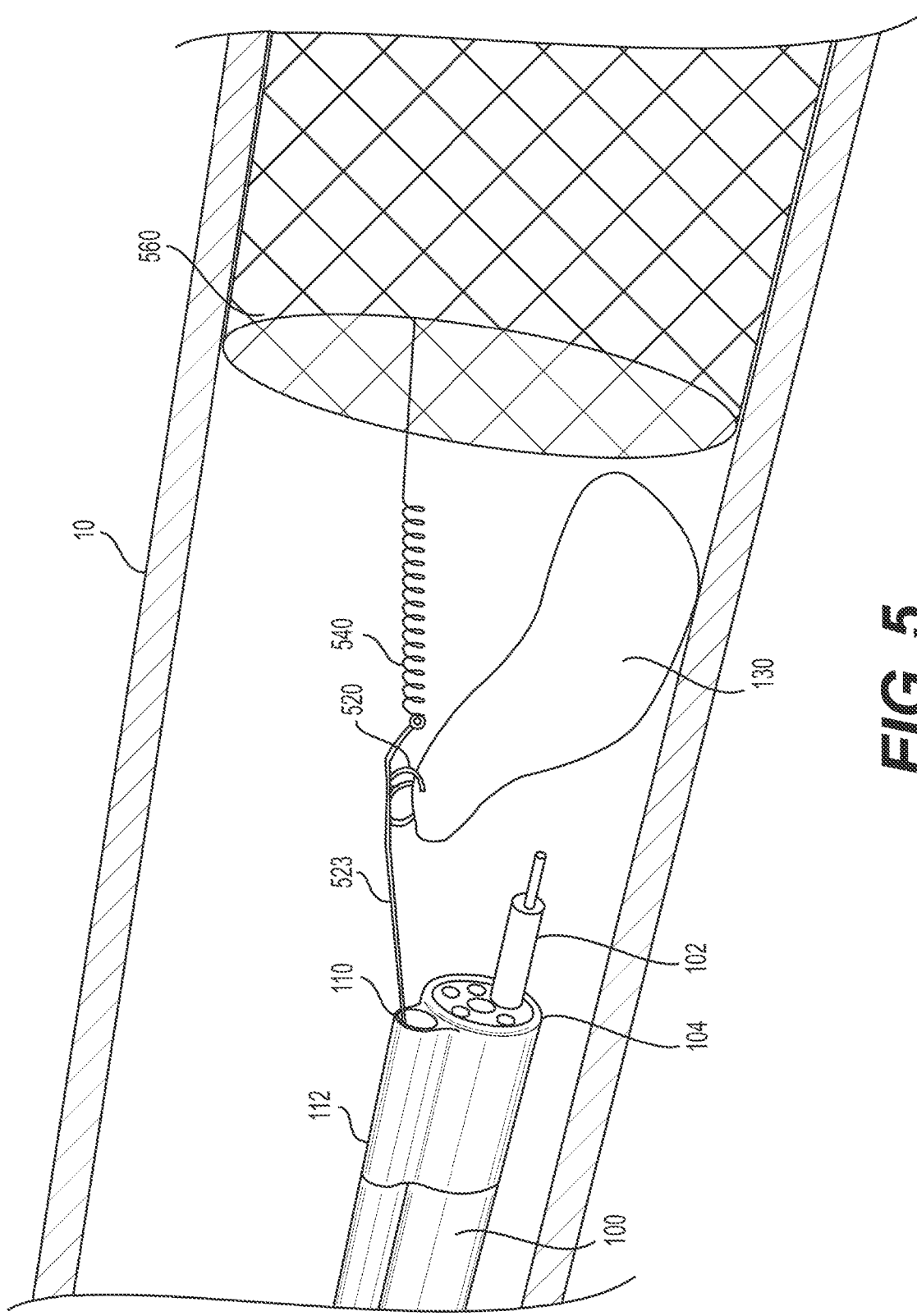
FIG. 5 illustrates an exemplary alternative retraction mechanism retracting a portion of the target tissue.

FIG. 5 illustrates an alternative example of anchoring a retraction mechanism to a body wall. In the example illustrated in FIG. 5, target tissue anchor 520 is a spiral loop similar to target tissue anchor 220 of FIGS. 2 and 3 and/or target tissue anchor 1120 of FIG. 11. Tension mechanism 540 may connect to stabilizing anchor 560 at a proximal region of stabilizing mechanism 560 and may connect to target tissue anchor 520 via wire 522. Tension mechanism 540 (e.g., a spring) may pull the previously-resection portion of target tissue 130 radially inward of the wall toward the body lumen and distally, e.g., toward tension mechanism 540. The spring may be any spring known in the art, including coil springs or elastomers made of any suitable biocompatible material. As previously mentioned, tension may be created in any way for any of the disclosed anchors. For example, FIG. 5 illustrates an example in which tension is created by a spring located distal of the retracted tissue and proximal of the stabilizing anchor. A spring, such as spring 540 of FIG. 5, may be used with any stabilizing anchor, including, but limited to the petal configuration of FIG. 3, the bulb configuration of FIG. 4, the stent of FIG. 5, the balloon of FIG. 6, and/or any other stabilizing anchor. It should be noted that in examples where the tension mechanism is a spring, only a single wire need extend through channel 110, because there is no need for an operator to provide tension. The amount of tension provided by tension mechanism 540 depends on the characteristics of tension mechanism 540 and the placement position of tension mechanism 540 relative to stabilizing anchor 560. Tension mechanism 540 may produce greater tension when stabilizing anchor 560 is placed further distally and less tension when stabilizing anchor 560 is placed further proximally.

Stabilizing anchor 560 may be a stent (e.g., any stent know in the art.) For example, stabilizing anchor 560 may be at least partially formed by a metal wire stent. Stabilizing anchor 560 may be configured to transition between a first contracted configuration (e.g., for insertion) and a second expanded configuration (e.g., once in a desired position relative to target tissue 130). Stabilizing anchor 560 may include any suitable self-expanding mesh or coil structure. For example, stabilizing anchor 560 may include a braided and/or twisted lattice of wire(s), a helical or semi-helical spiral, and/or a plurality of undulating, corrugated, or sinusoidal rings. Additionally, stabilizing anchor 560 may be made, at least partially, of a shape-memory material such as, for example, a Cobalt-Chromium-Nickel alloy like Elgiloy, synthetic plastics, stainless steel, and superelastic metallic alloys of Nickel and Titanium (e.g., nitinol), copper, cobalt, vanadium, chromium, iron, or the like. Alternative materials may include, but are not limited to, other metal alloys, powdered metals, ceramics, thermal plastic composites, ceramic composites, and polymers. Combinations of these and other materials may be used.

Figure 6:
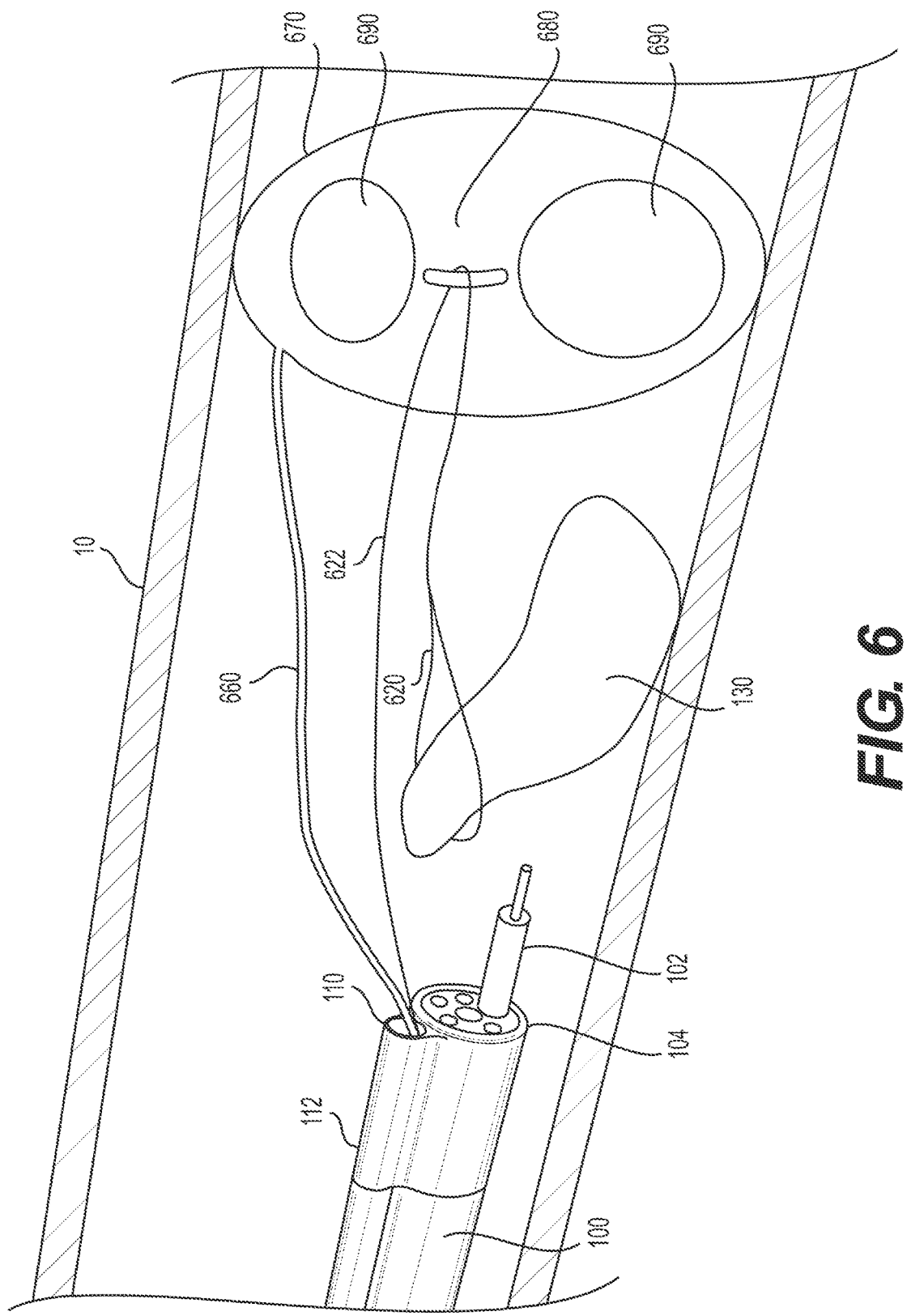
FIG. 6 illustrates an exemplary alternative retraction mechanism retracting a portion of the target tissue.

FIG. 6 illustrates an alternative example of anchoring a retraction mechanism to a body wall. In the example of FIG. 6, target tissue anchor 620 is a loop made of, for example, metal wire, plastic, and/or elastic material. Target tissue anchor 620 loops around the previously-resected portion of the target tissue 130. Target tissue anchor 620 may be looped around target tissue 130 in any way, including a grasping device (not shown) extending through a lumen of delivery device 100 to position target tissue anchor 620 around a proximal portion of target tissue 130. Target tissue anchor 620 may then attach to a first end of wire 622 and/or be formed of a first end of wire 622 connected to a more proximal portion. Wire 622 may be made of metal wire, plastic, and/or elastic material. Wire 622 may attach to stabilizing anchor 670. In the example illustrated in FIG. 6, wire 622 loops around connection device 680 and a second end of wire 622 may extend proximally from stabilizing anchor 670, into channel 110 and to the proximal end of overtube 112. The second end of wire 622 may provide an operator control over the amount of tension and/or the distance the previously-resected portion of target tissue 130 is pulled up (inward) and/or distally. For example, the more an operator proximally pulls the second end of wire 622, the further the already-resected portion of target tissue 130 will be pulled distally. Connection device 680 may be connected to or integral with stabilizing anchor 660. Connection device 680 may be, for example, a hook or a loop. Connection device 680 may be made of plastic, metal, elastomer, and/or the same material as the expandable member 670. In some examples, attachment device 680 may be coated, for example, by duraskin, a PTFE "Teflon" based material. Such a coating may allow wire 622 to slide more easily. In the example illustrated in FIG. 6, the loop (e.g., target tissue anchor 620) and/or wire 622 may act as the tension mechanism as well. The loop and/or wire 622 may be formed of an elastic material, thus, pulling the first end of wire 622 and/or the loop wrapped around the already-resected portion of target tissue 130 in an upward (radially inward) and distal direction.

Stabilizing anchor 670 may be an expandable member, such as an inflatable balloon. Stabilizing anchor 670 may be configured to transition between a first contracted configuration (e.g., for insertion through channel 110) and a second expanded configuration (e.g., distal of channel 110 and in a desired position relative to target tissue 130). Stabilizing anchor 670 may be fluidly connected to inflation lumen 660. Inflation lumen 660 may extend through channel 110 to a proximal end of delivery device 100 and may be connected to an inflation apparatus (not shown). Expandable member (stabilizing anchor) 670 may include one or more passage holes 690. Passage holes 690 may allow bodily fluids to pass through, while still anchoring the attached target tissue anchor. In some examples, expandable member 670 does not include a passage hole 690. In such examples, expandable member 670 may be disk-shaped or sphere-shaped in an expanded configuration.

Stabilizing anchor 670 may slide within channel 110 in an uninflated or contracted configuration. Once in a desired position (e.g., distal of target tissue 130), stabilizing anchor 670 may be expanded (e.g., inflated) via the introduction of a fluid through inflation lumen 660. Stabilizing anchor 670 may be expanded until it contacts and produces sufficient pressure against body wall 10 to resist proximal movement.

In addition to the retraction mechanisms discussed above, the stabilizing anchor may be anchored to a body wall in any way known in the art, including but not limited to a clip, hook, and/or screw. For example, the target tissue anchor may be a first clip attached to a portion of the tissue desired for retraction, and the stabilizing anchor may be a second clip attached to a body wall. The first clip and the second clip may be any clip known in the art.

2. Anchoring a Retraction Mechanism to a Delivery Device, Proximal an Articulation Section As previously mentioned, in some examples, the retraction mechanism may be anchored to the delivery device, proximal of the delivery device's articulation section. Such a configuration allows the distal end of the delivery device to move independently of the retraction mechanism. The articulation section may be a segment of the delivery device that permits the distal end of delivery device to articulate. The articulation section may be structured in any way known in the art, including, articulation joints, a transition to a more flexible material, and/or slots cut into the delivery device. The articulation section may be, for example, a plurality of articulation joints that pivot/bend relative to one another to allow the distal tip of the delivery device to sharply bend in up-down and left-right directions, similar to an endoscope distal tip. The articulation joints may be connected to an actuator at the proximal/operator end via one or more pull wires. The wires are pushed/pulled to bend the articulation section as desired. The portion of the delivery device proximal to the articulation section remains flexible to traverse tortuous anatomy, but may not include articulation joints or be actively articulable, and may be relative stiffer than the articulation section.

Figure 7A:
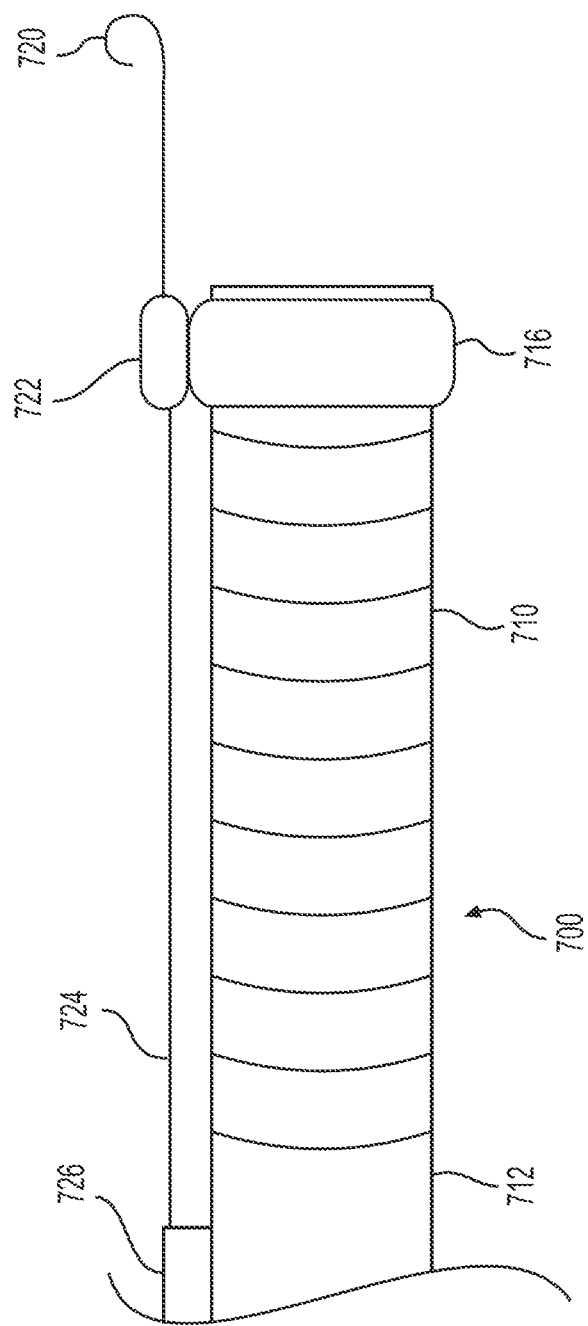
FIGS. 7A and B illustrate an exemplary delivery device having a retraction mechanism anchored to the delivery device proximal to an articulation section.

FIGS. 7A and B illustrate an exemplary delivery device 700 having a target tissue anchor 720 anchored to the delivery device 700, proximal to articulation section 710. In the examples illustrated in FIGS. 7A and B, delivery device 700 includes a proximal section 712 (e.g., proximal of articulation section 710) and a distal section 716. Distal section 716 may be integrally formed with delivery device 700 or distal section 716 may be a cap configured to attach to delivery device 700. Additionally or alternatively, delivery device 700 may include stabilizing anchor 726 (e.g., structure for securing wire 724 to proximal section 712 of delivery device 700, for example, a strap, fastener, crimp, an overtube, and/or dock 722. The distal end of wire 724 may form and/or be attached to target tissue anchor 720. In some examples, the distal end of wire 724 may form a spiral loop, like spiral loop 720 of FIG. 7A. An illustration of a deployment of a spiral loop-shaped target tissue anchor, like spiral loop 720, is described below with respect to FIGS. 11A-C.

FIG. 7A illustrates an insertion configuration of target tissue anchor 720 of delivery device 700. In FIG. 7A, dock 722 may be touching delivery device 700, or, more specifically, distal section 716. During insertion, dock 722 may be flush against the side of delivery device 700. Dock 722 and, as a result, wire 724 and target tissue anchor 720, may move in unison with delivery device 700.

FIG. 7B illustrates a retracting configuration of target tissue anchor 720 of delivery device 700. Once inserted and fastened to the target tissue (e.g., spiral loop 720 pierces at least a proximal portion of the target tissue as described further with respect to FIGS. 11A-C), target tissue anchor 720 may be transitioned to a retracting configuration. In one example, the operator may take action (e.g., press a button, provide a command to an operating computer, etc.) that releases dock 722 from delivery device 700. In some examples, dock 722, wire 724, and/or target tissue anchor 720 may be biased in an upward direction (e.g., away from delivery device 700). In one example, wire 724 may be made, at least partially, of a shape-memory material such as, for example, a Cobalt-Chromium-Nickel alloy like Elgiloy, synthetic plastics, stainless steel, and superelastic metallic alloys of Nickel and Titanium (e.g., nitinol), copper, cobalt, vanadium, chromium, iron, or the like. In another example, a spring (e.g. apparatus 728) may be positioned between dock 722 and delivery device 700. Thus, once dock 722 is no longer locked or otherwise held against to delivery device 700, the spring (e.g. apparatus 728) may bias dock 722 and target tissue anchor 720 away from delivery device 700. In some examples, the transition to a retracting configuration may be due to an actuator at the proximal/operator end via one or more pull wires. The wires are pushed/pulled to bend wire 724 as desired. For example, the operator may pull an attached wire that can steer target tissue anchor 720 away from delivery device 700 and/or may reattach dock 722 to delivery device 700. In some examples, apparatus 728 may be a tether and may extend to the proximal end of delivery device 700 to provide operator control. In such examples, target tissue anchor 720 may transition back to the insertion configuration by pulling apparatus 728 (e.g., the tether) in the proximal direction.

In some examples, element 724 may represent a tubular element. Target tissue anchor 720 may be an elongate wire, extending through a channel of tubular element 724. In such examples, tubular element 724 (and target tissue anchor 720 inside tubular element 724) may extend through and distally of dock 722 and into the field of view of any imaging apparatuses of delivery device 700. With a distal end of tubular element 724 within the field of view, an operator may accurately position the device relative to target tissue and/or observe the deployment of a distal end of target tissue anchor 720. Similar to the above description of wire 724 transitioning away from delivery device 700 distal of stabilizing anchor 726, tubular element 724 may also transition away in any way known in the art.

Figure 8A:
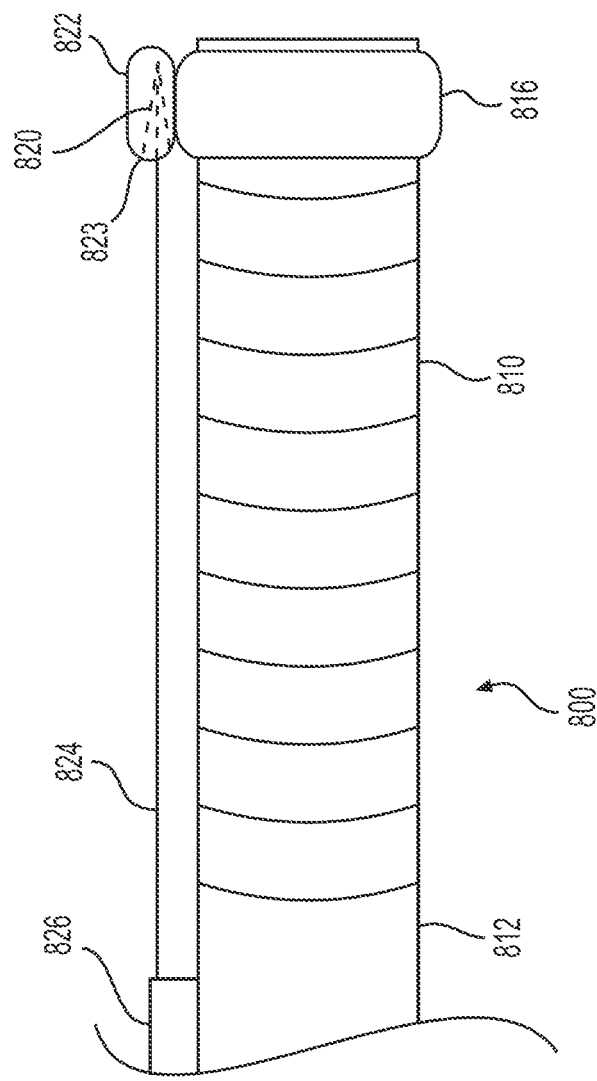
FIGS. 8A and B illustrate an alternative exemplary delivery device having a retraction mechanism anchored to the delivery device proximal to an articulation section.

FIGS. 8A and B illustrate an alternative exemplary delivery device 800 having a target tissue anchor 820 anchored to the delivery device, proximal to articulation section 810. In the example illustrated in FIGS. 8A and B, delivery device 800 includes a proximal section 812 (e.g., proximal of articulation section 810) and a distal section 816. Distal section 816 may be integrally formed with delivery device 800 or distal section 816 may be a cap configured to attach to delivery device 800. Additionally or alternatively, delivery device 800 may include stabilizing anchor 826 (e.g., any structure for securing wire 824 to proximal section 812 of delivery device 800 and/or dock 822. Dock 822 may include a proximal-facing cavity 823. The distal end of tether/wire 824 may form and/or be attached to a target tissue anchor. In some examples, the distal end of wire 824 may attach to a grasper, like grasper 820 of FIG. 8A. Proximal-facing cavity 823 of dock 822 may be sized, shaped, or otherwise configured so that a distal end of a target tissue anchor may be disposed and/or locked inside of cavity 823.

FIG. 8A illustrates an insertion configuration of target tissue anchor 820 of delivery device 800. In FIG. 8A, dock 822 may be fixedly attached to delivery device 800, or, more specifically, distal section 816. During insertion, target tissue anchor 820 may be locked and/or disposed within a cavity of dock 822 (e.g., proximal-facing cavity 823). Thus, during insertion of delivery device 800, wire 824 and target tissue anchor 820 may move in unison with delivery device 800.

FIG. 8B illustrates a retracting configuration of target tissue anchor 820 of delivery device 800. Once removed from dock 822, target tissue anchor 822 may be transitioned to a retracting configuration. In one example, the operator may take action (e.g., press a button, provide a command to an operating computer, etc.) to release target tissue anchor 820 from dock 822 of delivery device 800. In some examples, target tissue anchor 820 may be biased in an upward direction (e.g., away from delivery device 800). The device of FIGS. 8A and B may use any of the biasing mechanisms and/or steering mechanisms described above with respect to FIGS. 7A and B and/or any other biasing/steering mechanisms known in the art. For example, tether/wire 824 may slidably extend through stabilizing anchor 826 and along delivery device 800 to a proximal actuator outside the body. The operator may push/pull or otherwise activate the actuator to release target tissue anchor 822. The proximal actuator also may include a mechanism for steering target tissue anchor 820 toward target tissue and/or another mechanism for activating target tissue anchor 820 to grasp target tissue.

Figure 9A:
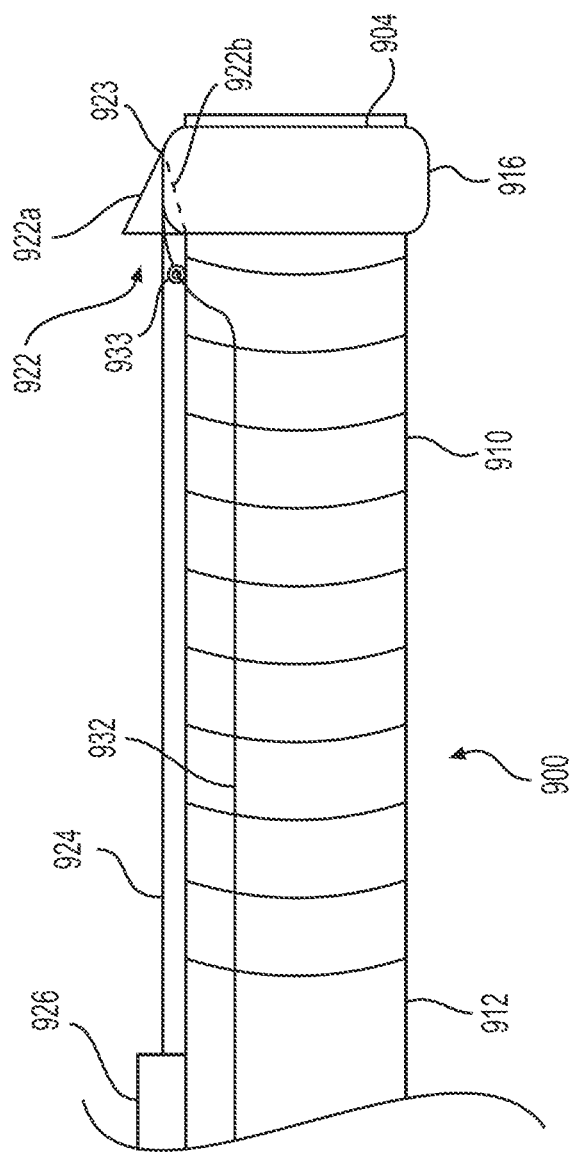

FIGS. 9A-C illustrate an alternative exemplary delivery device 900 having a target tissue anchor 922 anchored to the delivery device proximal to articulation section 910. Delivery device 900 may include stabilizing anchor 926 (e.g., any structure for securing wire 924 to proximal section 912 of delivery device 900). The distal end of tether or wire 924 may attach to and/or form a target tissue anchor. In some examples, the distal end of wire 924 may attach to a grasper, like grasper 922 of FIG. 9A. Grasper 922 may include arms 922a (e.g., the arm opposite delivery device 900 when in the insertion configuration) and 922b (e.g., the arm adjacent/closest to delivery device 900 when in the insertion configuration). In some examples, delivery device 900 includes a proximal section 912 (e.g., proximal of articulation section 910), distal end 904, and a distal section 916. Distal section 916 may be integrally formed with delivery device 900 or distal section 916 may be a cap configured to attach to delivery device 900. Distal section 916 may include a mating feature, e.g., dovetail feature 923. Dovetail feature 923 captures at least a portion of target tissue anchor 922 (e.g., grasper arm 922b) in order to secure grasper 922 during navigation of delivery device 900. Though a dovetail feature is illustrated, any mating structure known in the art may be used to secure target tissue anchor 922 to distal section 916.

FIG. 9B illustrates a retracting configuration of target tissue anchor 922 of delivery device 900. Once the distal end 904 of delivery device 900 is inserted in the patient and positioned proximate to the target tissue, the operator may release tissue target tissue anchor 922. In one example, wire 932 at its distal end may be attached to target tissue anchor 922 and at its proximal end to an activator/handle for use by an operator. Wire 932 may be secured through eyelet 933 to delivery device 900. Eyelet 933 may be, for example, a loop protruding radially outward from delivery device 900. The operator may pull wire 932 proximally, and thus release target tissue anchor 922 from dovetail feature 923. Wire 932 may then be used to steer and/or re-insert target tissue anchor 922 into dovetail feature 923. In some examples, target tissue anchor 922 may be biased in an upward direction (e.g., radially outward from delivery device 900). The device of FIGS. 9A and B may use any of the biasing/steering mechanisms described with respect to FIGS. 7A and B and/or any other biasing/steering mechanisms disclosed in this disclosure or otherwise known in the art.

FIG. 9C depicts a proximal-facing view of distal end 904 of delivery device 900. Dovetail feature 923 secures a mating feature of grasper arm 922b. As shown here, delivery device 900 may additionally include one or more working channel(s).

Figure 10A:
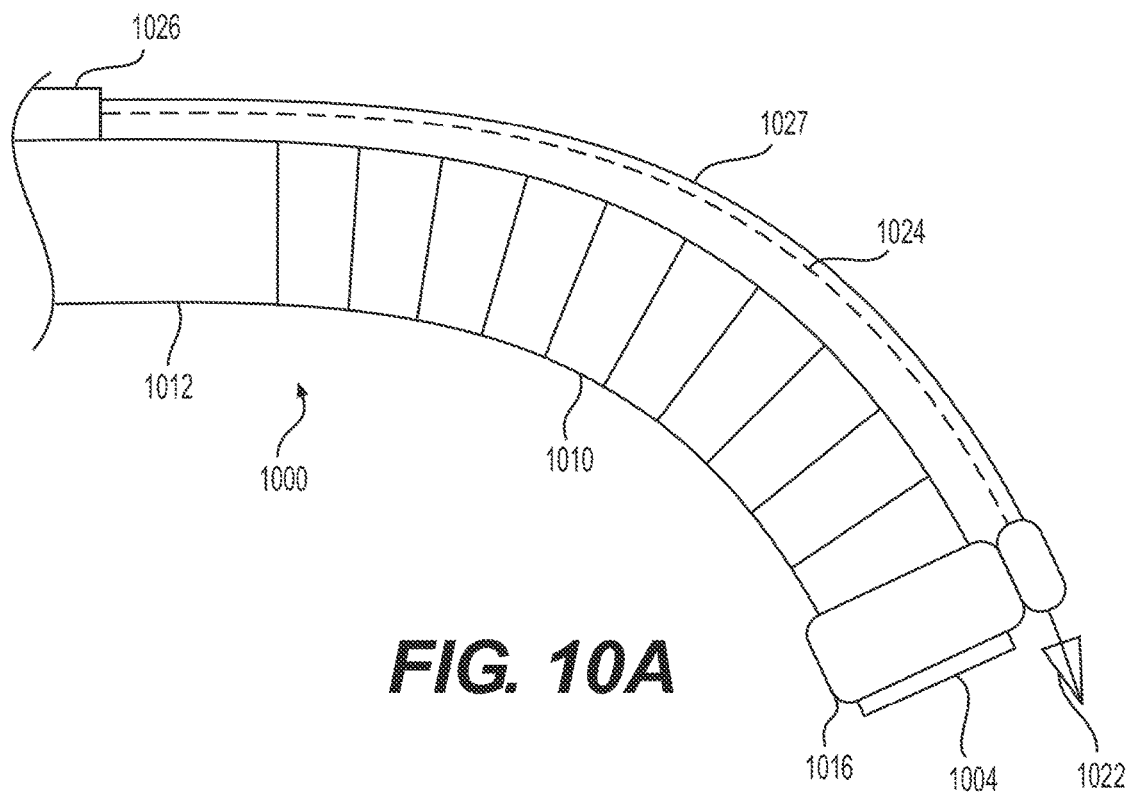
FIGS. 10A and B illustrate an alternative exemplary delivery device having a retraction mechanism anchored to the delivery device proximal to an articulation section.

FIGS. 10A and B illustrate an alternative exemplary delivery device 1000 having a retraction mechanism anchored to the delivery device proximal to articulation section 1010. In some examples, delivery device 1000 includes a proximal section 1012 (e.g., proximal of articulation section 1010) and a dock 1016. Dock 1016 may be slidably disposed around delivery device 1000. Dock 1016 may be connected to a stabilizing anchor 1026 via sleeve 1027. Sleeve 1027 may be made from any suitable biocompatible material known to one of ordinary skill in the art and having sufficient flexibility to traverse tortuous anatomy with delivery device 1000. Sleeve 1027 may be any width, thickness, and/or shape. For example, sleeve 1027 may be a single strip of flexible material extending between stabilizing anchor 1026 and dock 1016. In some examples, sleeve 1027 may wrap around delivery device 1000, covering a full 360 degrees (e.g., completely encircling delivery device 1000) of the outer surface of delivery device 1000.

The distal end of tether/wire 1024 may attach to and/or form a target tissue anchor. In some examples, the distal end of wire 1024 may attach to a grasper, like grasper 1022 of FIGS. 10A-B.

FIG. 10A illustrates an insertion configuration of delivery device 1000. During insertion, as shown in FIG. 10A, the target tissue anchor (e.g., grasper 1022) may be secured against delivery device 1000 at or near distal end 1004 by dock 1016. During insertion of delivery device 1000, wire 1024, sleeve 1027, and target tissue anchor 1022 may move in unison with delivery device 1000.

Figure 10B:
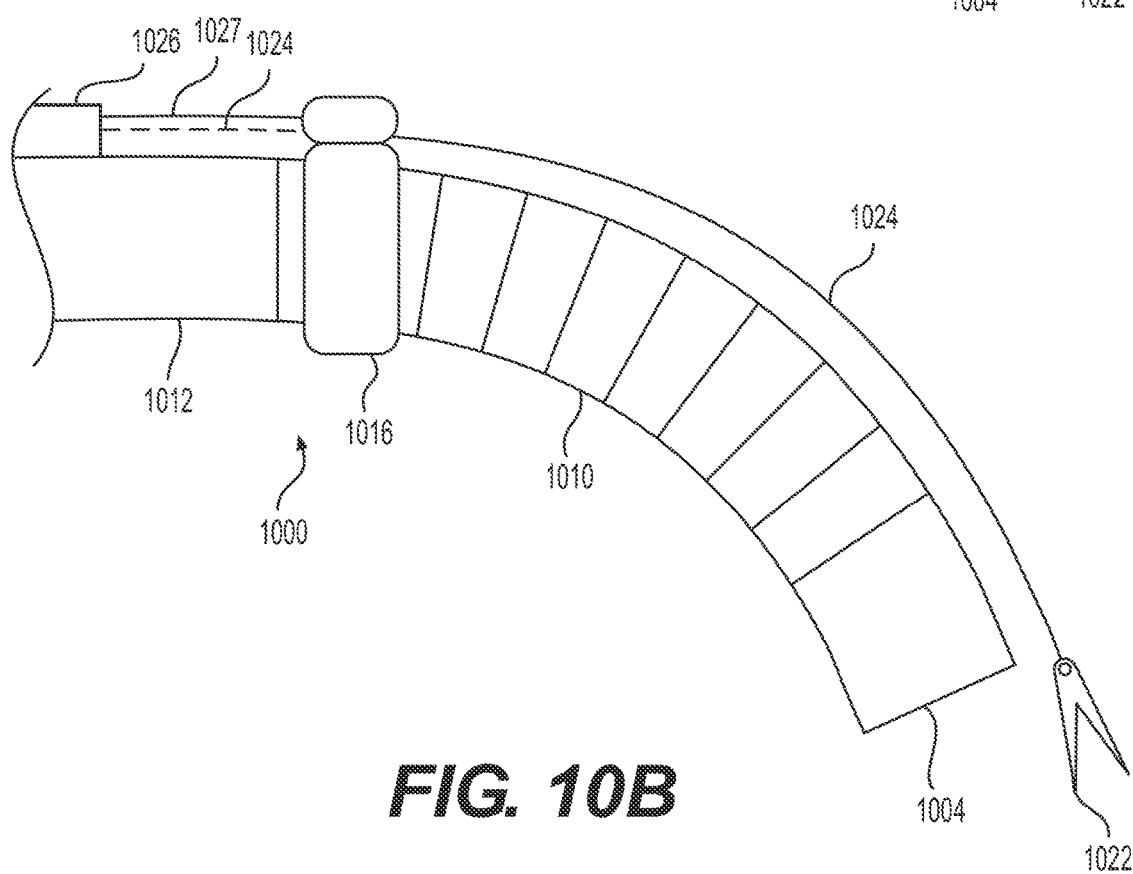

FIG. 10B illustrates a retracting configuration of target tissue anchor (e.g., grasper 1022) of delivery device 1000. Once the distal end 1004 of delivery device 1000 is inserted in the patient and positioned proximate to the target tissue, the operator may release target tissue anchor (e.g., grasper 1022). In one example, a pull wire may be used to pull dock 1016, as well as sleeve 1027, in the proximal direction, leaving target tissue anchor (e.g., grasper 1022) free from restraint. Target tissue anchor (e.g., grasper 1022) may be released before or after grasper 1022 fastens to the target tissue. In some examples, target tissue anchor (e.g., grasper 1022) may be biased in an upward direction (e.g., radially outward from delivery device 1000). The device of FIGS. 10A and B may use any of the biasing/steering mechanisms described with respect to FIGS. 7A and B and/or any other biasing/steering mechanisms otherwise disclosed in this disclosure or known in the art. In some examples, a steering mechanism, such as a wire, may be used to steer target tissue anchor (e.g., grasper 1022). Some examples may not include stabilizing anchor 1026. For example, once dock 1016 is pulled proximal of articulation section 1010, dock 1016 may act as a stabilizing anchor.

FIGS. 11A-C illustrate an exemplary target tissue anchor 1120 transitioning from an insertion configuration to an engaged configuration. The target tissue anchor 1120 may be used with any of the tension mechanisms and/or stabilizing anchors described above. Delivery device 1100 may include a dock 1122, a wire 1124, and a target tissue anchor 1120. Wire 1124 includes a distal end 1118 and distal end 1118 may be configured to pierce tissue (e.g., a sharpened tip). Delivery device 1100 may be positioned so that the dock 1122 is proximate to the target tissue. Wire 1124 may be in a constricted or straight configuration as it passing through a constraining element, e.g., dock 1122 or channel 110 of FIG. 3. FIG. 11A illustrates distal end 1118 following extension of wire 1124 distally of dock 1122 and distal end 1104. At this point, wire 1124 remains in the straight configuration. FIG. 11B illustrates further distal extension of wire 1124. Distal end 1118 may begin to curl (as shown in FIG. 11B) and form a spiral loop-shaped target tissue anchor 1120. FIG. 11C illustrates even further distal extension of wire 1124. Distal end 1118 may continue to curl (as shown in FIG. 11C) and form a hook, spiral loop, or corkscrew-shaped target tissue anchor 1120. Curling of distal end 1118 may be due to, for example, energy stored in the tissue anchor, inherent radial biasing, deformation due to body heat, or the like. In some examples, wire 1124 may be made, at least partially, of a shape-memory material such as, for example, a Cobalt-Chromium-Nickel alloy like Elgiloy, synthetic plastics, stainless steel, and superelastic metallic alloys of Nickel and Titanium (e.g., nitinol), copper, cobalt, vanadium, chromium, iron, or the like. In some examples, as distal end 1118 curls, the sharpened tip may pierce the target tissue, thus securing the target tissue. Further, in some examples, the energy stored in the tissue anchor, from being constrained by the constraining element, would be harvested to penetrate through tissue positioned just distal to the opening of the tube and gather the target tissue. A downward (or radially outward) flexure of the delivery device may provide pressure at the distal opening of the constraining element such that there is sufficient reactive force. Thus, when the target tissue anchor is projected distally from the constraining element, the target tissue anchor may penetrate into and/or fully encompass a portion of the target tissue. Once the tissue has been attached or gathered to the target tissue anchor, the target tissue anchor may be retracted. Alternatively, in some examples, the target tissue anchor may release the target tissue by, for example, reversing the process. A target tissue anchor in the engaged configuration may be withdrawn into the constraining element, e.g., dock 1122 or tube 111, resulting in a transformation into the straight configuration.

In some examples, the constraining element (e.g., dock 1122 or tube 111) may be configured to and/or capable of projecting distally of the distal end of the delivery device (e.g., distal end 1104 of delivery device 110 or distal end 104 of delivery device 100). The constraining element may be positioned within the field of view of the delivery device. This positioning may provide an operator with visual confirmation of the target tissue and the deployment of the target tissue anchor.

In some examples, both stabilizing anchor positions may be used, e.g., a retraction mechanism may be anchored to both a delivery device proximal of the articulation section and to a body wall. This may provide for additional stabilization of the target tissue anchor and/or for the resection of target tissue.

A. Anchoring to a Retroflexed Delivery Device

In some implementations, an operator may wish to retroflex the delivery device. For example, as shown in FIG. 12A, the distal end 104 of delivery device 1200 may be inserted distally beyond target tissue 130, and then distal end 104 may be looped around to retroflex delivery device 1200 and point distal end 104 (and any imaging devices thereon) proximally at target tissue 130. In these examples, the entire length of delivery device 1200 may be flexible enough to retroflex. In other examples, deliver device 1200 may include an articulation section, e.g., articulation section 1201 having a length less than the entire length of the delivery device 1200. As previously mentioned, such an articulation section may be in a distal portion of the delivery device and/or a retraction mechanism may be attached to the delivery device proximally of said articulation section. Such a configuration allows the distal end of the delivery device to move independently of the retraction mechanism. The articulation section may be a segment of the delivery device that permits the distal end of delivery device to articulate. The articulation section may be structured in any way known in the art, including, articulation joints, a transition to a more flexible material, and/or slots cut into a portion of the delivery device to permit additional flexibility. The articulation section may be, for example, a plurality of articulation joints that pivot/bend relative to one another to allow the distal tip of the delivery device to sharply bend in up-down and left-right directions, similar to an endoscope distal tip. The articulation joints may be connected to an actuator at the proximal/operator end via one or more pull wires. The wires are pushed/pulled to bend the articulation section as desired. The portion of the delivery device proximal to the articulation section remains flexible to traverse tortuous anatomy, but may not include articulation joints or be actively articulable, and may be relatively stiffer than the articulation section. FIGS. 12A-17B illustrate retroflexed delivery devices in which the retraction mechanism is anchored to the delivery device, proximal of the delivery device's articulation section.

Figure 12B:
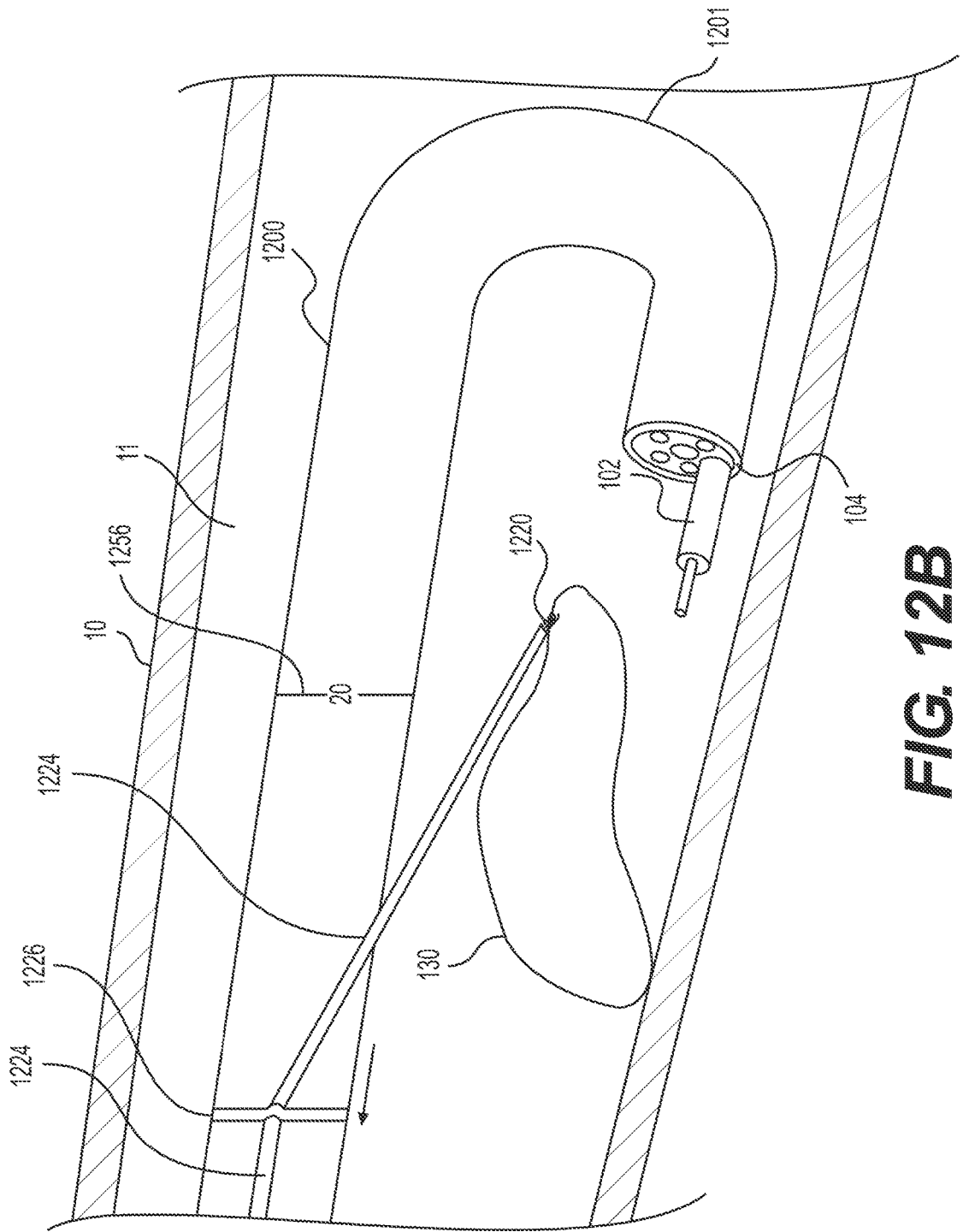
Figure 12C:
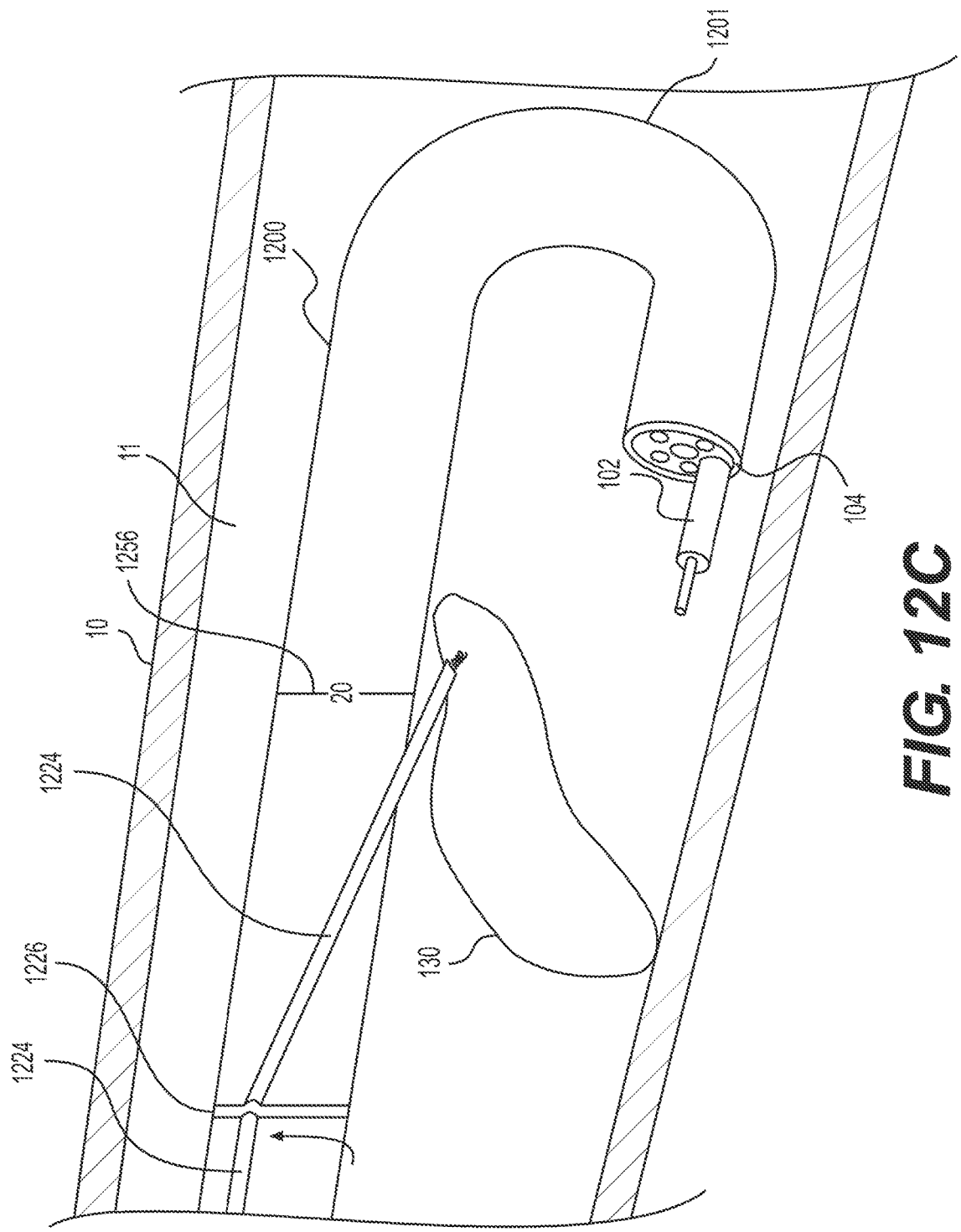

FIGS. 12A-C illustrate an exemplary retroflexed delivery device 1200 having a retraction mechanism anchored to the delivery device 1200, proximal to articulation section 1201. The exterior of delivery device 1200 may include one or more markers 1256 for indicating distance from the proximal and/or distal end of delivery device 1200. For example, as illustrated in FIGS. 12A-C and 13A-B, marker 1256 reads "20," and thus indicates 20 cm from the distal end of delivery device 1200. In the examples illustrated in FIGS. 12A-C, delivery device 1200 may include stabilizing anchor 1226 (e.g., structure for securing elongate member 1224 to a section of delivery device 1200 proximal to articulation section 1201). For example, stabilizing anchor 1226 may be a slidable band, strap, fastener, ring, overtube, etc. positioned about the exterior of the delivery device 1200.

Elongate member 1224 may be any member capable of exerting a force (e.g., away from the body wall) on target tissue 130 (e.g., upward in FIG. 12A) and/or any member capable of extending to a proximal end of delivery device 1200. In some examples, elongate member 1224 may be a rod or a wire. The distal end of elongate member 1224 may form and/or be attached to target tissue anchor 1220. Target tissue anchor 1220 may be any mechanism capable of grasping, securing, and/or manipulating tissue, including any such mechanism described herein. For example, as shown in FIG. 12A, target tissue anchor 1220 may be a corkscrew having a tip to secure to target tissue 130. In such an example, a wire may extend through a hollow, elongate member 1224 and have a proximalmost end that extends to an operator at a proximal end of delivery device 1200. The distalmost end of the wire may be pre-formed as a corkscrew or may be made, at least partially, of a shape-memory material, so that once the distalmost end exits elongate member 1224 and/or once the distalmost end enters a patient's body, it may transition from a straight configuration to a corkscrew-like shape (as shown in FIG. 12A). The corkscrew may have a sharp or pointed distalmost end. An operator may rotate a proximalmost end of the attached wire, thus rotating the corkscrew-like shape at the distalmost end and essentially screwing target tissue anchor 1220 into target tissue 130.

In an insertion configuration (not shown), target tissue anchor 1220 and elongate member 1224 may be flush against the side of delivery device 1200 and move in unison with delivery device 1200. Any releasable securing mechanism known in the art may be used to secure the portion of elongate member 1224 that is distal to stabilizing anchor 1226 to delivery device 1200.

FIG. 12A illustrates a connection configuration of target tissue anchor 1220 of delivery device 1200. In FIG. 12A, the operator may take action (e.g., press a button, move a portion of a handle or actuator, provide a command to an operating computer, etc.) that at least partially releases target tissue anchor 1220 and/or elongate member 1224 (e.g., a portion distal to stabilizing anchor 1226) from the side of delivery device 1200. In some examples, elongate member 1224 and/or target tissue anchor 1220 may be biased in a direction toward the direction that delivery device 1200 retroflexes/articulates (e.g., away from delivery device 1200 and/or toward target tissue 130; downward in FIG. 12A). In one example, elongate member 1224 may be made, at least partially, of a shape-memory material such as, for example, a Cobalt-Chromium-Nickel alloy like Elgiloy, synthetic plastics, stainless steel, and superelastic metallic alloys of Nickel and Titanium (e.g., nitinol), copper, cobalt, vanadium, chromium, iron, or the like. In another example, a spring (not shown) may be positioned between elongate member 1224 and delivery device 1200, distal of stabilizing anchor 1226. Thus, once a distal portion of elongate member 1224 is no longer locked or otherwise held or positioned against or adjacent to delivery device 1200, the spring may bias the distal portion of elongate member 1224 and target tissue anchor 1220 away from delivery device 1200. In some examples, the transition to a connection configuration may be due to an actuator at the proximal/operator end via one or more pull wires. The wires are pushed/pulled to bend elongate member 1224 as desired. For example, the operator may pull an attached wire that can steer target tissue anchor 1220 away from delivery device 1200.

FIG. 12B illustrates a first retracting configuration of target tissue anchor 1220 of delivery device 1200. Once inserted and fastened to the target tissue (e.g., the distal corkscrew pierces at least a portion of the target tissue as described above), target tissue anchor 1220 may be transitioned to a retracting configuration. In one example, the operator may take action (e.g., pull a proximal end of elongate member 1224, press a button, provide a command to an operating computer, etc.) that pulls stabilizing anchor 1226 proximally, thus pulling target tissue anchor 1220 and the portion of the target tissue 130 connected to target tissue anchor 1220 in a proximal and/or upward direction. In some examples, an operator may hold the already-resected portions of target tissue 130 at this retracted position. In other examples, an operator may rotate stabilizing anchor 1226 relative to delivery device 1200 (e.g., away from target tissue 130). FIG. 12C illustrates a second retracting configuration where stabilizing anchor 1226 was first pulled proximally (FIG. 12B) and then rotated counterclockwise when viewed from a proximal end (FIG. 12C) to achieve additional retraction and upward lift of target tissue 130.

Figure 13A:
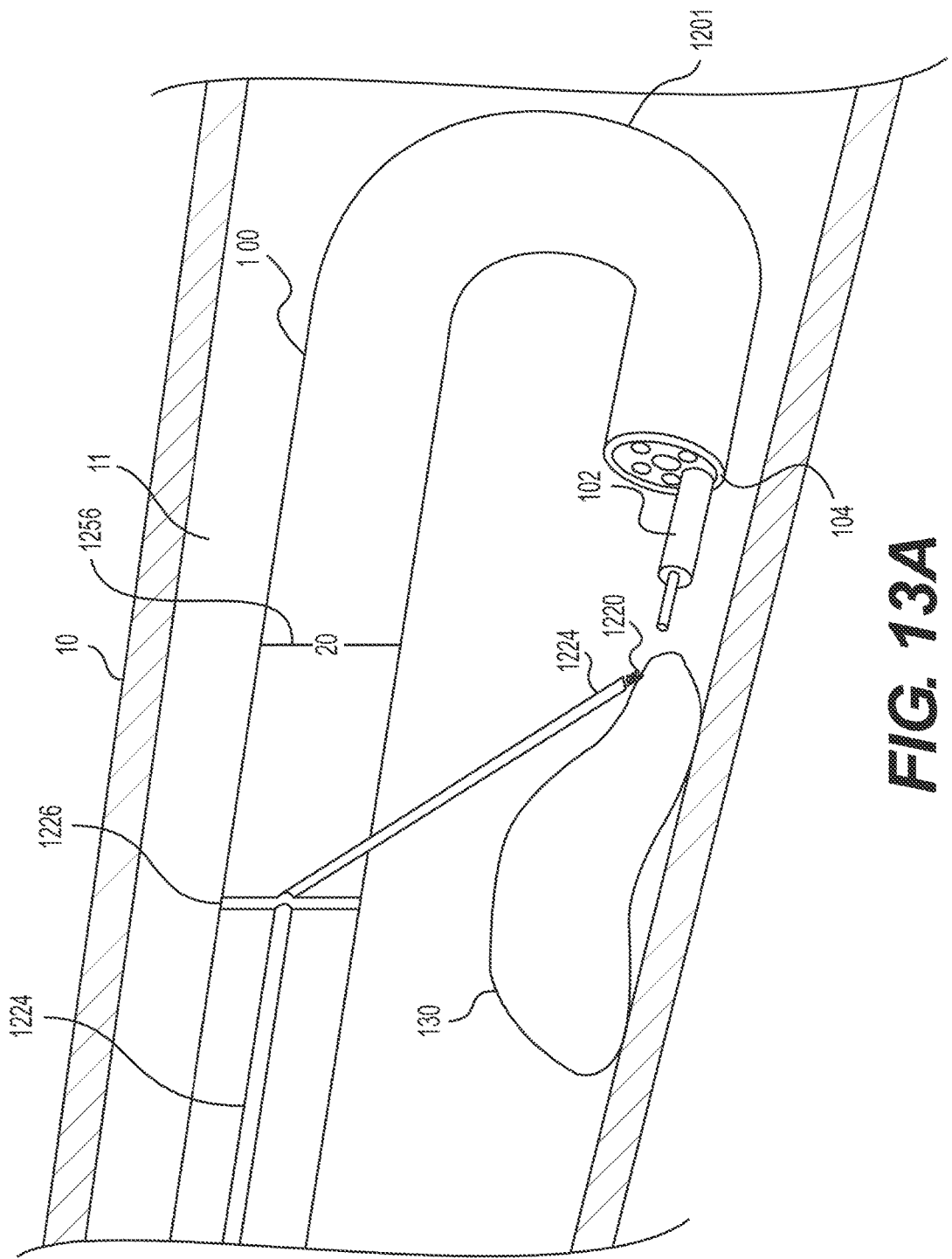
FIGS. 13A and B illustrate an alternative exemplary retroflexed delivery device having a retraction mechanism anchored to the delivery device proximal to an articulation section.
Figure 13B:
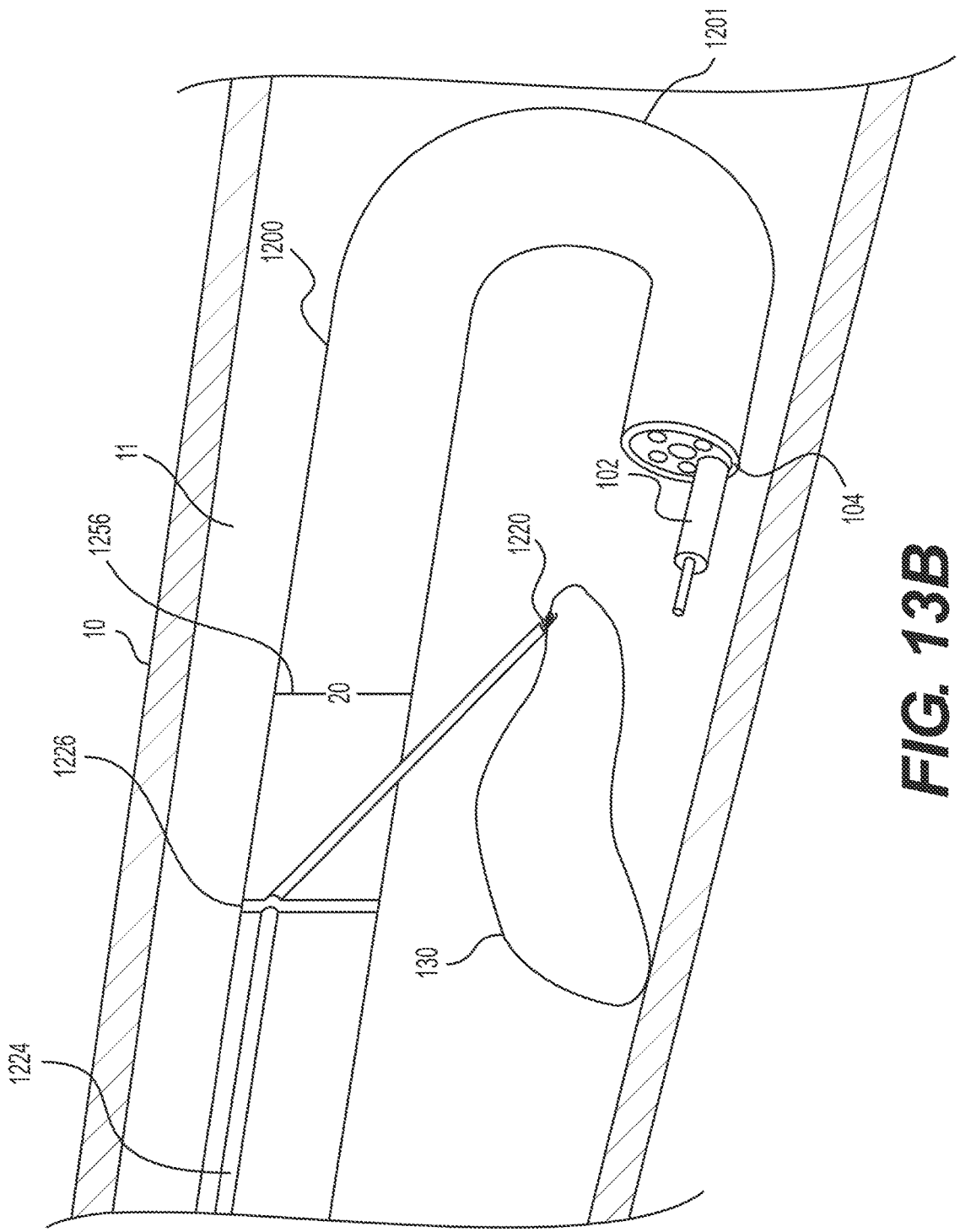

FIGS. 13A-B illustrate the same delivery device 1200 as FIGS. 12-C, but a different method of retracting. In the example illustrated in FIG. 13A, target tissue anchor 1220 of delivery device 1200 is in the connection configuration. A portion of target tissue anchor 1220 distal to stabilizing anchor 1226 has, in any way known in the art, been released from the side of delivery device 1200 and is angled in a downward direction (e.g., away from delivery device 1200 and/or toward target tissue 130). FIG. 13B illustrates a retracting configuration of target tissue anchor 1220 of delivery device 1200. Once inserted and fastened to the target tissue (e.g., the distal corkscrew pierces at least a proximal portion of the target tissue as described above), target tissue anchor 1220 may be transitioned to a retracting configuration. In this example, instead of pulling stabilizing anchor 1226 proximally (FIG. 12B), the operator rotates a proximal end of a mechanism (not shown) that extends from stabilizing anchor 1226 to a proximal end of delivery device 1200. Stabilizing anchor 1226 may remain in substantially the same longitudinal position relative to the distal and proximal ends of delivery device 1200, but may rotate in the same direction as this mechanism. Rotating stabilizing anchor 1226 may, in turn, rotate elongate member 1224 about delivery device 1200's outer surface, target tissue anchor 1220 away from the tissue wall adjacent target tissue 130, and lifting this portion of target tissue 130 up and away from the tissue wall.

Figure 14A:
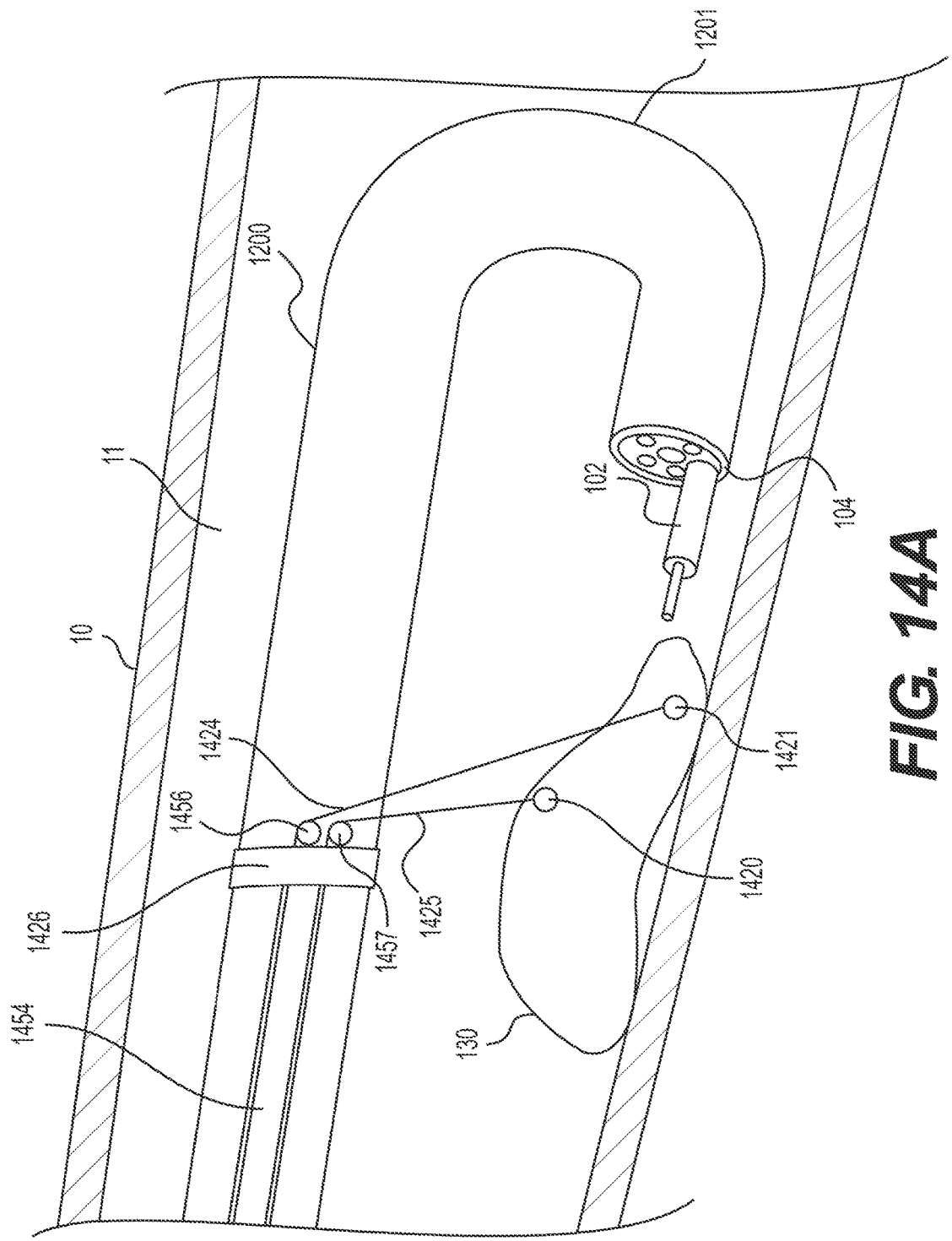
FIGS. 14A and B illustrate an alternative exemplary retroflexed delivery device having a retraction mechanism anchored to the delivery device proximal to an articulation section.
Figure 14B:
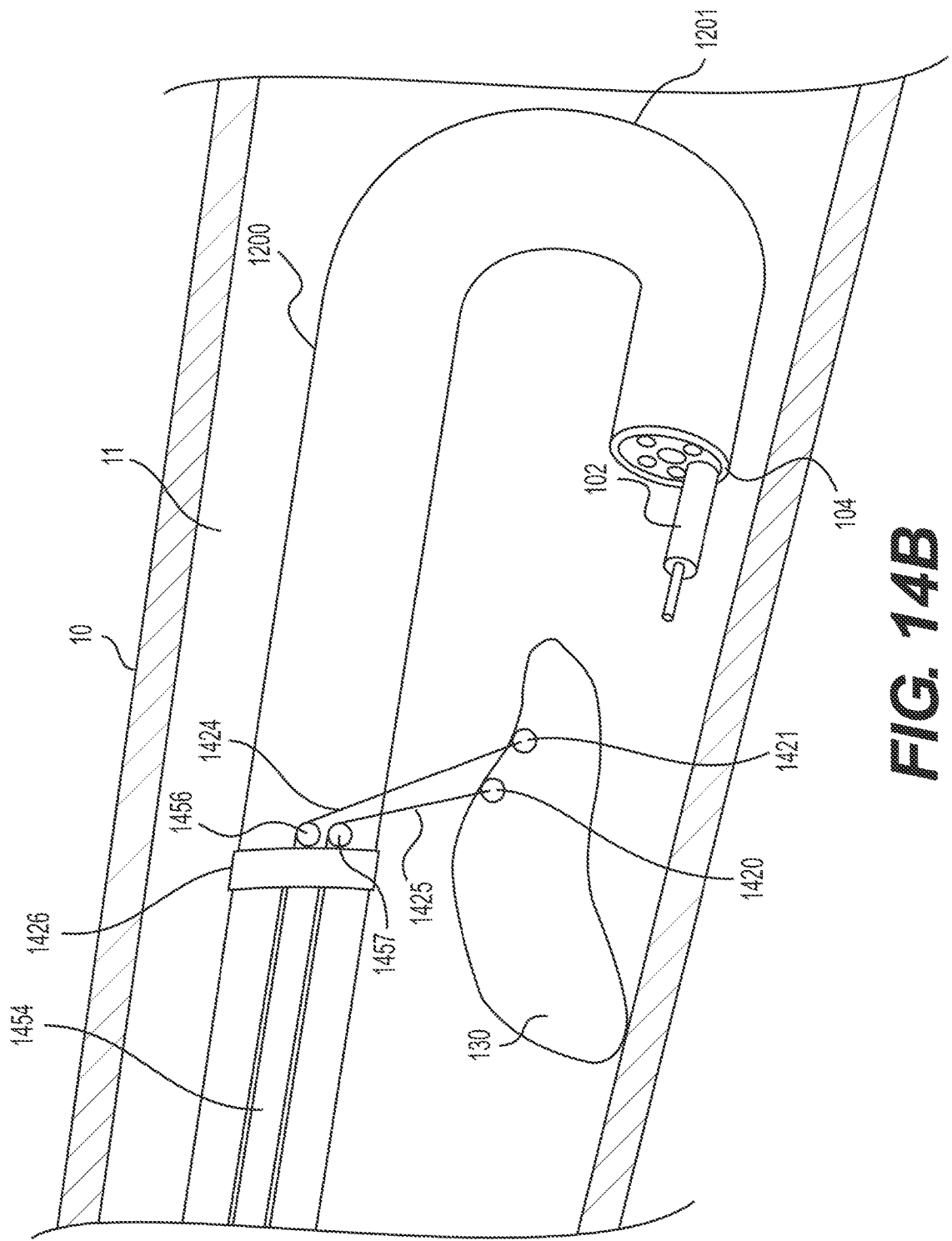

FIGS. 14A-B illustrate retroflexed device 1200 with a dual pulley system for retracting already-resected portions of target tissue 130. FIG. 14A illustrates a connection configuration of the dual pulley system, where target tissue 130 is not yet retracted. FIG. 14B illustrates a retracting configuration of the dual pulley system, where at least a portion of target tissue 130 is being retracted (e.g., held in an upward direction and/or away from the attached patient tissue wall).

The dual pulley system may include pulleys 1456 and 1457, an elongate member 1454 having a lumen therethrough (like a tube or channel), and stabilizing anchor 1426. Stabilizing anchor 1426 (e.g., structure for securing or positioning pulleys 1456 and 1457 to an exterior section of delivery device 1200 proximal to articulation section 1201) may be a band, strap, fastener, crimp, overtube, etc. In the example shown in FIGS. 14A and B, the dual pulley system may include wire 1424. The distal end of wire 1424 may form and/or be attached to target tissue anchor 1421. Target tissue anchor 1421 may be any mechanism capable of grasping, securing, and/or manipulating tissue, including any such mechanism described herein. Wire 1424 may loop around and ride over the pulley 1456 and extend through hollow, elongate member 1454 to an operator-controlled, proximal end of delivery device 1200. Similarly, the dual pulley system may include wire 1425. The distal end of wire 1425 may form and/or be attached to target tissue anchor 1420. Target tissue anchor 1420 may be any mechanism capable of grasping, securing, and/or manipulating tissue, including any such mechanism described herein. Wire 1425 may loop around and ride over the pulley 1457 and extend through hollow, elongate member 1454 to an operator-controlled, proximal end of delivery device 1200. To transition the dual pulley system from a connection configuration to a retracting configuration (e.g., from FIG. 14A to 14B), and thus lift at least a portion of target tissue 130, one or both of wires 1424 and 1425 may be pulled in a proximal direction. In some examples, wires 1424 and 1425 may be pulled an equal distance and with equal force. In some examples, one wire may be pulled harder and/or farther than the other. For example, in order to provide a greater working area closer to distal end 104 of delivery device 1200, wire 1424 (e.g., the wire connected to the tissue anchor 1421 which is closer to distal end 104 of delivery device 1200) may be pulled harder or farther than wire 1425 and thus, the portion of tissue closest to distal end 104 of delivery device 1200 may be lifted higher than other retracted portions. The system may include any number of pulleys. For example, the system may include a single wire and a single pulley or the system may include more than two pulleys and two wires.

Figure 15A:
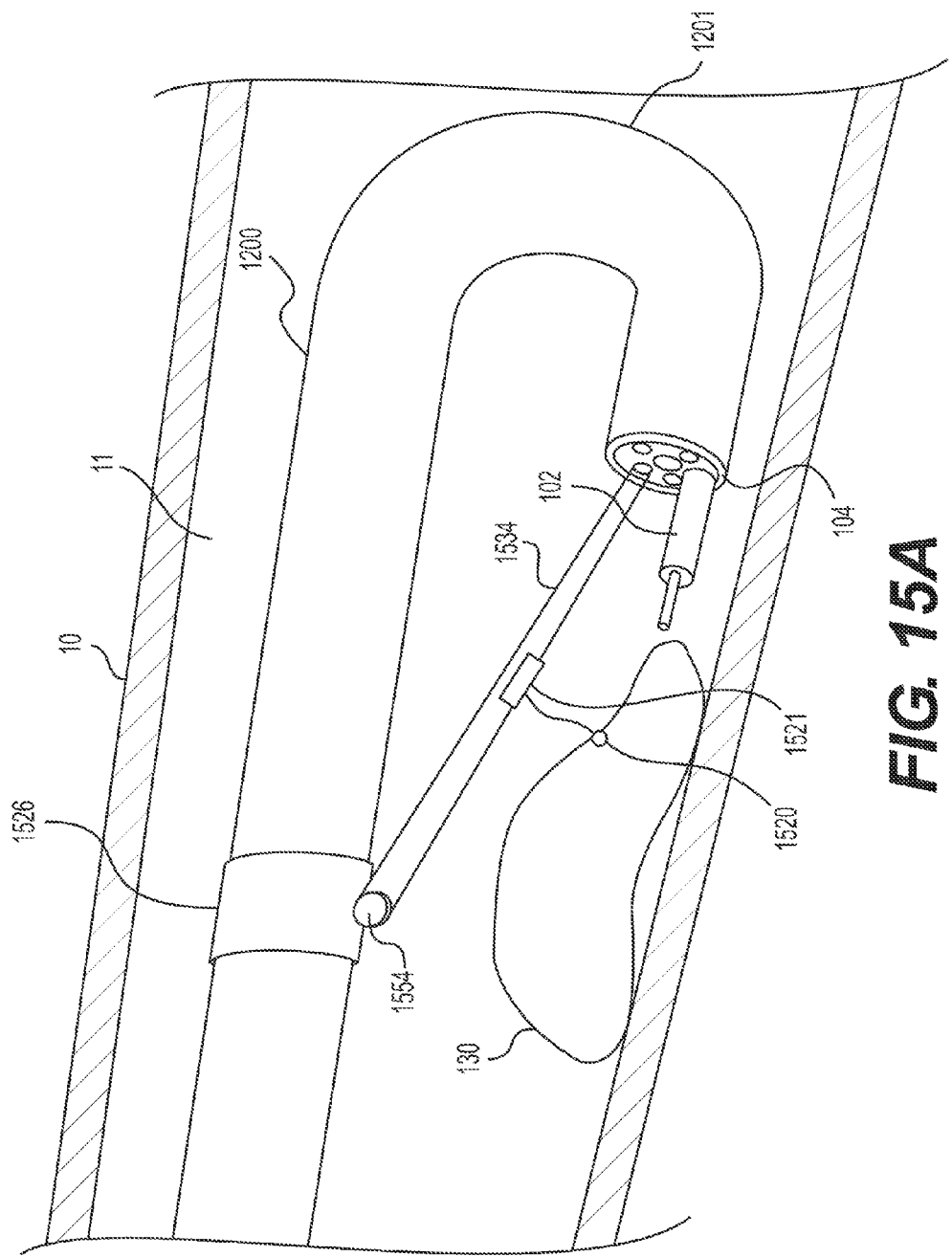
FIGS. 15A and B illustrate an alternative exemplary retroflexed delivery device having a retraction mechanism anchored to the delivery device proximal to an articulation section.
Figure 15B:
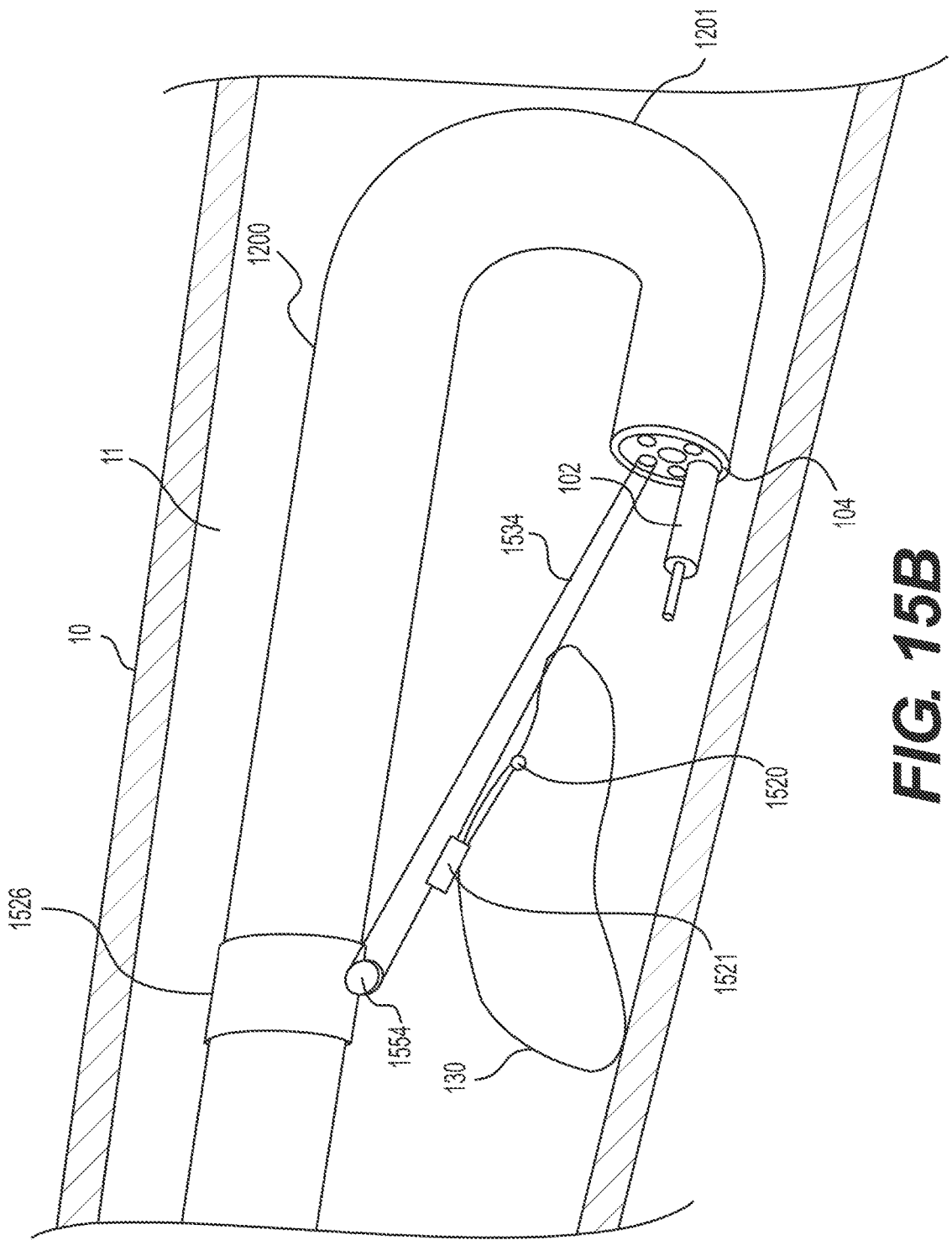

FIGS. 15A-B illustrate retroflexed device 1200 with a taut-line system (e.g., similar in design to a traditional clothes lines) for retracting resected portions of target tissue 130. FIG. 15A illustrates a connection configuration of the taut-line system, where target tissue 130 is not yet retracted/lifted. FIG. 15B illustrates a retracting configuration of the taut-line system, where at least a portion of target tissue 130 is being retracted/lifted (e.g., held in an upward direction and/or away from the attached patient tissue wall).

The taut-line system may include stabilizing anchor 1526, pulley 1554, a wire 1534, and a connector 1521. Stabilizing anchor 1526 (e.g., structure for securing or positioning pulley 1554 adjacent to an exterior section of delivery device 1200 and proximal to articulation section 1201) may be a band, strap, fastener, crimp, overtube, ring, etc. The wire 1534 may loop around and ride over the pulley 1554 may extend through one or more of the working channel(s) of delivery device 1200 to an operator-controlled, proximal end of delivery device 1200. The two ends of the wire 1534 may be located at the proximal end of delivery device 1200 for pushing/pulling by an operator. The wire 1534 may include a connector 1521. In other examples, the taut-line system may include two connectors at different positions on wire 1534. In some examples, connector 1521 may be configured to attach and/or fasten to target tissue 130. In the example illustrated in FIGS. 15A and B, connector 1521 connects target tissue anchor 1520 to the wire 1534. Target tissue anchor 1520 may be any mechanism capable of grasping, securing, and/or manipulating tissue, including any such mechanism described herein. To transition the taut-line system from a connection configuration to a retracting configuration (e.g., from FIG. 15A to FIG. 15B), and thus lift at least a portion of target tissue 130, one end of the wire 1534 may be pulled in a proximal direction to pull connector 1521, tissue anchor 1520, and the fastened portion of target tissue 130 toward stabilizing anchor 1526 and away from the patient tissue wall.

FIGS. 16A-D illustrate an exemplary delivery device 1600 and an exemplary method of inserting and retroflexing delivery device 1600. Stabilizing anchor 1626 may be radially outward of and slidable over delivery device 1600. Stabilizing anchor 1626 may be connected to and controlled by wire 1625. Wire 1625 may extend to an operator-controlled, proximal end of delivery device 1600. Stabilizing anchor 1626 may also be connected (e.g., via a wire 1610) to target tissue anchor 1620. Target tissue anchor 1620 may be any mechanism capable of grasping, securing, and/or manipulating tissue, including any such mechanism described herein.

Figure 16A:
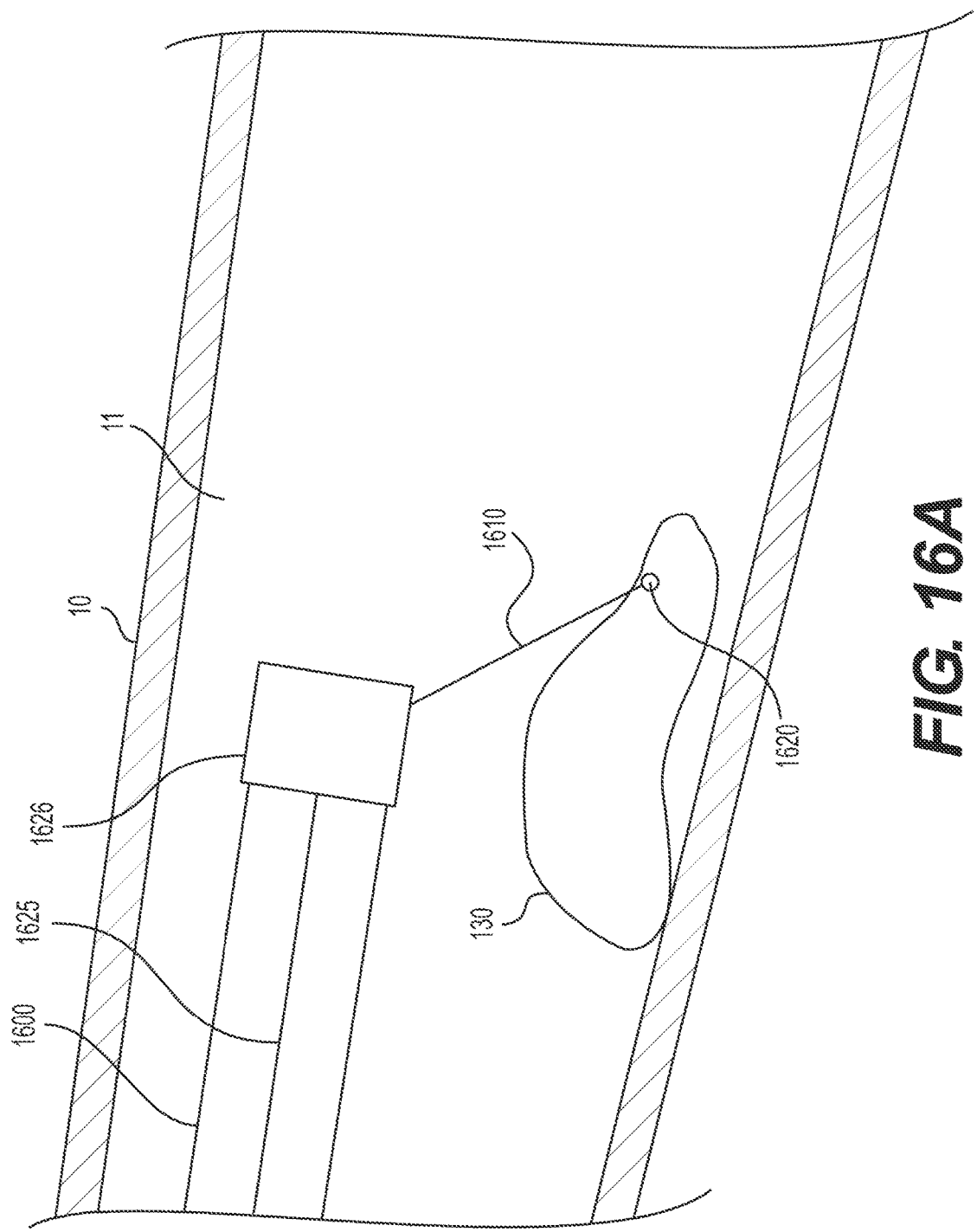
FIGS. 16A-D illustrate an alternative exemplary retroflexed delivery device having a retraction mechanism anchored to the delivery device proximal to an articulation section.
Figure 16B:
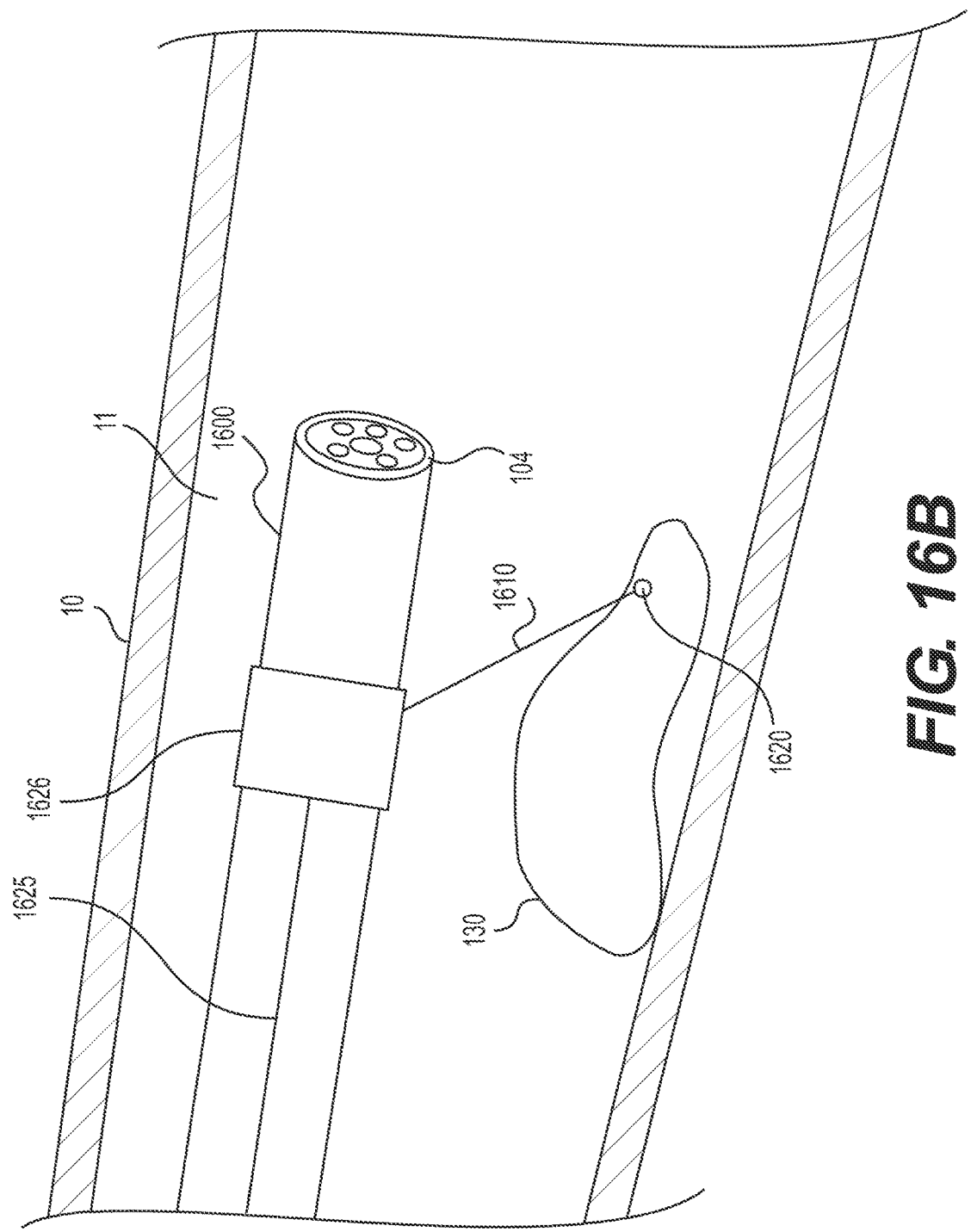
Figure 16C:
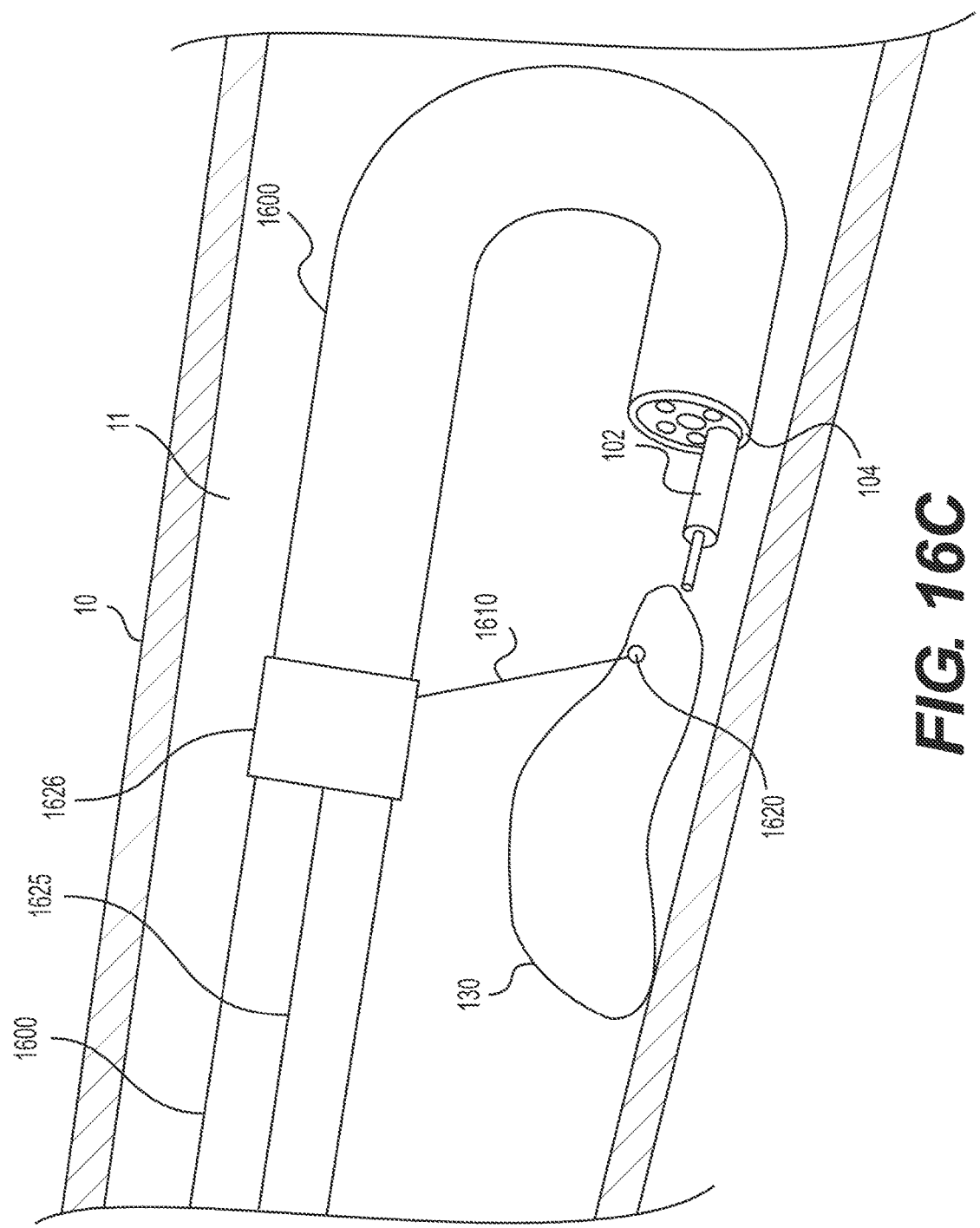
Figure 16D:
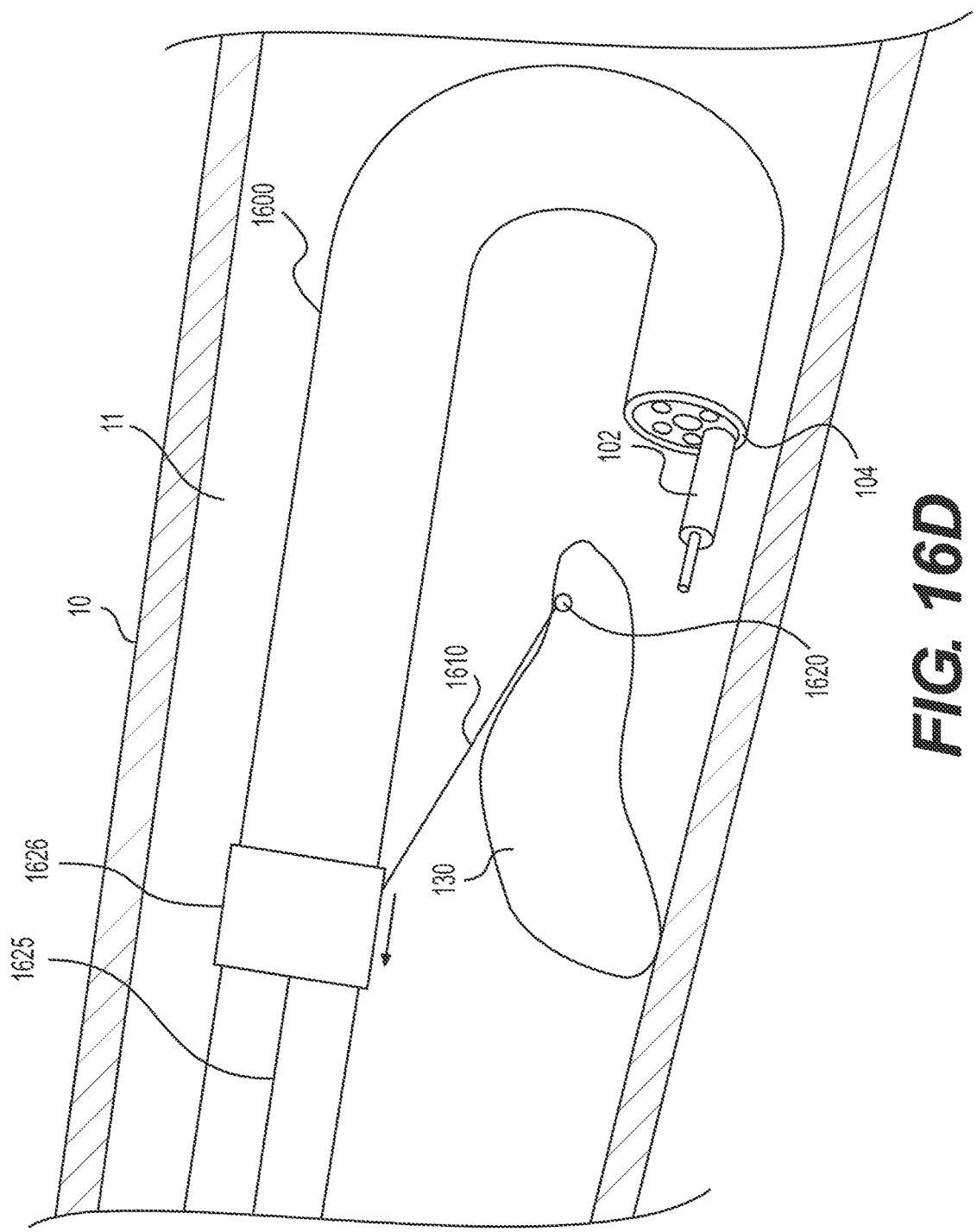

FIG. 16A illustrates an insertion configuration. Stabilizing anchor 1626 is disposed at or near the distal end of delivery device 1600. Once the distal end of delivery device 1600 and/or stabilizing anchor 1626 reach target tissue 130, target tissue anchor 1620 may be deployed and fastened to the target tissue 130 in any way known in the art or described herein. Once in a desired position, stabilizing anchor 1626 may remain in substantially the same location relative to body wall 10, even as delivery device 1600 moves distally. This may be accomplished in any way known in the art, including, but not limited to, securing the proximal end of wire 1625. FIG. 16B illustrates distal end 104 of delivery device 1600 extending distally of stabilizing anchor 1626. FIG. 16C illustrates delivery device 1600 extending further distally and retroflexing, while stabilizing anchor 1626 remains in substantially the same location relative to body wall 10. Once delivery device 1600 is in the desired position and/or medical instrument 102 resects at least a portion of target tissue 130, stabilizing anchor 1626 may be transitioned to a retracting configuration. FIG. 16D illustrates delivery device 1600 in the retroflexed position of FIG. 16C with the stabilizing anchor 1626 in the retracting configuration. Stabilizing anchor 1626 may be transitioned to a retracting configuration by pulling a proximal end of wire 1625 proximally and thus moving stabilizing anchor 1626 proximally. Moving stabilizing anchor 1626 proximally pulls target tissue anchor 1620 and the portion of target tissue 130 already-resected in an upward direction, toward stabilizing anchor 1626 and away from the tissue wall.

Figure 17A:
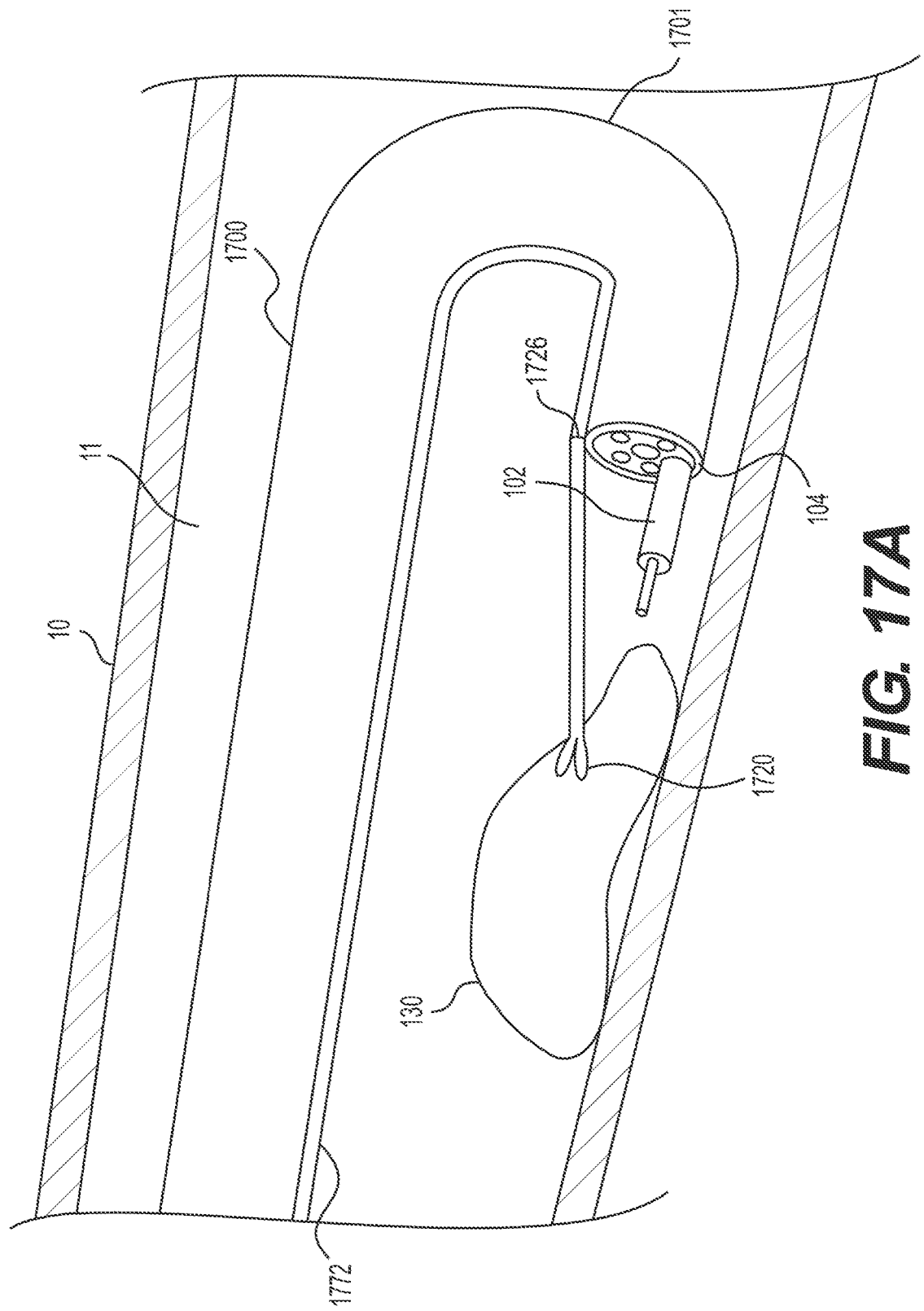
FIGS. 17A and B illustrate an alternative exemplary retroflexed delivery device having a retraction mechanism extending through a channel in the delivery device.

FIGS. 17A and B illustrate an alternative exemplary retroflexed delivery device 1700 having a retraction mechanism anchored to the delivery device 1700, proximal to articulation section 1701. Delivery device 1700 includes channel 1772. Channel 1772 may define a hollow lumen of any suitable shape, including, for example, a C-shape, U-shape, and/or V-shape. Channel 1772 may extend from a proximal end (not shown) of delivery device 1700 to distal end 104 of delivery device 1700. A target tissue anchor 1720, and its attached elongate member portion, may extend/slide through channel 1772. In an insertion configuration and a connection configuration (as explained in more detail below), the portion of channel 1772 distal of stabilizing anchor 1726 may be configured in any way to prevent movement of target tissue anchor 1720 and its elongate member portion radially outward of channel 1772 until a desired time. For example, a desired time may be upon intervention by an operator or control system and/or when transitioning from a connection configuration to a retracting configuration. At such a point, channel 1772 may be altered to allow radially outward movement of target tissue anchor 1720 and a distal portion of its attached elongate member. In some examples, the portion of a wall of channel 1772 distal of stabilizing anchor 1726 may include one or more of a longitudinal slit extending to the distal end of channel 1772 and having abutting edges; a longitudinal flap extending to the distal end of channel 1772 and having overlapping edges; interlocking longitudinal edges; a frangible longitudinal portion; or a layer of material disposed in-between target tissue anchor 1720 and its elongate member and the exterior of the channel, wherein the layer is thinned or weakened enough to promote tearing or perforation, or is a generally soft material for providing a weak wall through which target tissue anchor 1720 and its attached elongate member can be pushed/pulled.

Target tissue anchor 1720 may be any mechanism capable of grasping, securing, and/or manipulating tissue, including any such mechanism described herein. For example, as shown in FIG. 17A, target tissue anchor 1720 may be a grasper connected to a distal end of an attached elongate member.

In an insertion configuration (not shown), the distal end (e.g., the grasper portion) of target tissue anchor 1720 may remain within channel 1772 and/or be proximal of distal end 104 of delivery device 1700. Once at a desired position, the distal end (e.g., the grasper portion) of target tissue anchor 1720 may extend out of channel 1772 and connect/attach/fasten to a portion of target tissue 130. FIG. 17A illustrates such a connection configuration of target tissue anchor 1720 of delivery device 1700.

Figure 17B:
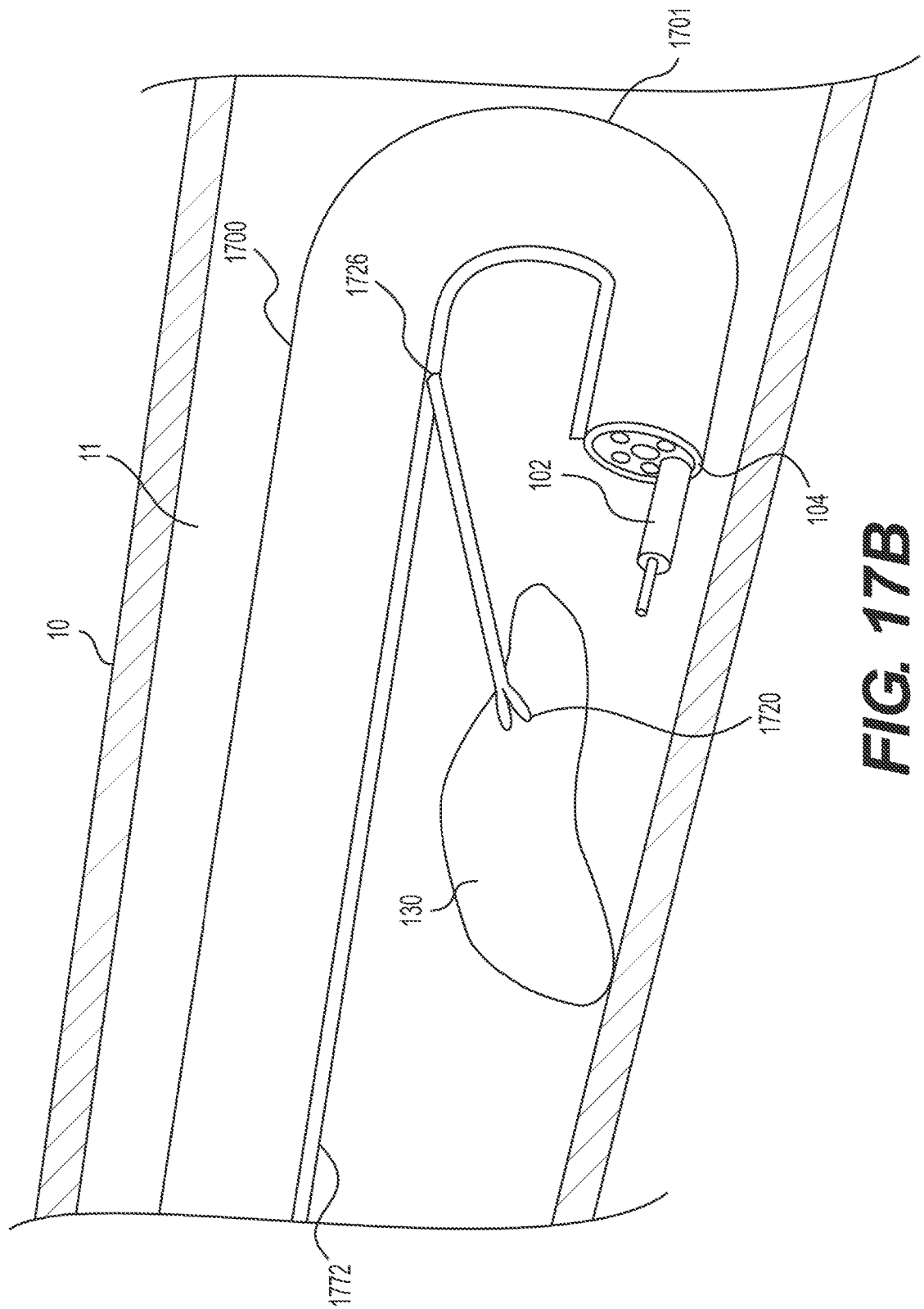

FIG. 17B illustrates a retracting configuration of target tissue anchor 1720 of delivery device 1700. In FIG. 17B, the operator may take action (e.g., press a button, provide a command to an operating computer, push or pull on a wire or other actuation mechanism, etc.) that at least partially releases target tissue anchor 1720 and a portion of its attached elongate member (e.g., a portion distal of stabilizing anchor 1726) from channel 1772 of delivery device 1700. For example, a wire may be pulled that tears (or unzips) a perforation in a wall of channel 1772. In another example, a wire may control a proximal end of target tissue anchor 1720 and pulling this wire may create sufficient force on a wall of channel 1772 to allow a length of target tissue anchor 1720 to access the exterior.

In some examples, the elongate member portion of target tissue anchor 1720 may be biased in an upward direction (e.g., away from delivery device 1700 and/or out of channel 1772). In one example, the elongate member of target tissue anchor 1720 may be made, at least partially, of a shape-memory material such as, for example, a Cobalt-Chromium-Nickel alloy like Elgiloy, synthetic plastics, stainless steel, and superelastic metallic alloys of Nickel and Titanium (e.g., nitinol), copper, cobalt, vanadium, chromium, iron, or the like. By releasing target tissue anchor 1720 from channel 1772 distal to stabilizing anchor 1726, target tissue anchor 1720 may pull upward and thus, lift already-resected portions of target tissue 130.

In some examples, the elongate member of target tissue anchor 1720 may articulate. For example, the elongate member of target tissue anchor 1720 may be structured in any way known in the art, including articulation joints, a transition to a more flexible material, and/or slots cut into the elongate member of target tissue anchor 1720. The elongate member of target tissue anchor 1720 may be, for example, a plurality of articulation joints that pivot/bend relative to one another. The articulation joints may be connected to an actuator at the proximal/operator end via one or more pull wires. The wires are pushed/pulled to bend the elongate member of target tissue anchor 1720 as desired.

At a certain distance proximal of distal end 104 of delivery device 1700, the channel 1772 may prevent radially outward movement even in a retracting configuration. For example, stabilizing anchor 1726 may be a portion of channel 1772 securing proximal portions of target tissue anchor 1720. Stabilizing anchor 1726 may secure proximal portions of target tissue anchor 1720 in any way. For example, stabilizing anchor 1726 may be a ring exterior to or embedded within delivery device 1700. Stabilizing anchor 1726 may be a non-weakened, stronger portion of channel 1772, or may be a stronger layer of material disposed between target tissue anchor 1720 and the exterior of the channel. In the example shown In FIGS. 17A and B, stabilizing anchor 1726 may be proximal of articulation section 1701.

Embodiments of the present disclosure may be used in any medical procedure, including any medical procedure where resection of a layer of targeted tissue is required. In addition, at least certain aspects of the above-mentioned embodiments may be combined with other aspects of the embodiments, or removed, without departing from the scope of the disclosure.

Other embodiments of the disclosure will be apparent to those skilled in the art from consideration of the specification and practice of the disclosure disclosed herein. It is intended that the specification and examples be considered as exemplary only, with a true scope and spirit of the disclosure being indicated by the following claims.

What is claimed is:

1. A medical instrument comprising:
   a delivery device; and
   a retractor including a target tissue anchor and a stabilizing anchor;
   wherein the target tissue anchor is adapted to attach to target tissue, wherein the target tissue anchor connects to the delivery device and the stabilizing anchor, wherein the stabilizing anchor is adapted to contact tissue distal the target tissue at a plurality of points, and wherein the stabilizing anchor is adapted to remain in one location relative to a body wall of a patient while a tension mechanism is adapted to pull the target tissue toward the stabilizing anchor and away from the body wall.

2. The medical instrument of claim 1, wherein the tension mechanism connects the target tissue anchor and the stabilizing anchor, wherein the tension mechanism includes at least one of a spring, a string, a wire, a rod, a pulley, and an elastic band.

3. The medical instrument of claim 1, wherein the delivery device includes an overtube and the retractor is at least partially disposed in the overtube.

4. The medical instrument of claim 1, wherein the stabilizing anchor has an expanded configuration and a contracted configuration.

5. The medical instrument of claim 1, wherein the stabilizing anchor is one of an inflatable balloon or an expandable structure comprised of a plurality of wires.

6. The medical instrument of claim 1, wherein the target tissue anchor includes one of a clip, a suture, a corkscrew, a spike, a hook, a grasper, a staple, an adhesive, a loop, a spiral loop, or a helical loop.

7. The medical instrument of claim 1, wherein the target tissue anchor connects to a proximal end of the delivery device.

8. The medical instrument of claim 1, wherein the delivery device is adapted to deliver a cutting instrument configured to cut the target tissue, and the retractor is adapted to pull a portion of the target tissue away from a body wall of a patient.

9. A retractor comprising:
   a target tissue anchor, wherein the target tissue anchor is adapted to attach to target tissue;
   a stabilizing anchor, wherein the stabilizing anchor has an expanded configuration and a contracted configuration and is adapted to contact tissue distal the target tissue at a plurality of points; and
   a tension mechanism connecting the target tissue anchor and the stabilizing anchor;
   wherein, in the expanded configuration, the stabilizing anchor is adapted to remain in one location relative to a body wall of a patient, and the tension mechanism is adapted to pull the target tissue toward the stabilizing anchor and away from the body wall.

10. The retractor of claim 9, wherein the stabilizing anchor is one of an inflatable balloon or an expandable structure comprised of a plurality of wires.

* * * * *